(12) United States Patent
Alamin et al.

(10) Patent No.: US 10,864,022 B2
(45) Date of Patent: *Dec. 15, 2020

(54) METHODS AND APPARATUS FOR COUPLING A PROSTHESIS TO A SPINAL SEGMENT

(71) Applicant: Empirical Spine, Inc., Woodside, CA (US)

(72) Inventors: Todd Alamin, Woodside, CA (US); Manish Kothari, San Carlos, CA (US); Hugues Malandain, Mountain View, CA (US); Colin Cahill, Portola Valley, CA (US); Louis Fielding, San Carlos, CA (US)

(73) Assignee: Empirical Spine, Inc., Woodside, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/148,907

(22) Filed: Oct. 1, 2018

(65) Prior Publication Data

US 2019/0029735 A1    Jan. 31, 2019

Related U.S. Application Data

(63) Continuation of application No. 15/397,611, filed on Jan. 3, 2017, now Pat. No. 10,092,331, which is a
(Continued)

(51) Int. Cl.
*A61B 17/00* (2006.01)
*A61B 17/70* (2006.01)

(52) U.S. Cl.
CPC ...... *A61B 17/7067* (2013.01); *A61B 17/7053* (2013.01); *A61B 17/7055* (2013.01); *A61B 17/7062* (2013.01); *A61B 2017/00725* (2013.01)

(58) Field of Classification Search
CPC ............ A61B 17/7067; A61B 17/7053; A61B 17/7055; A61B 17/7062; A61B 17/7011;
(Continued)

(56) References Cited

U.S. PATENT DOCUMENTS 3,648,691 A    3/1972  William et al.
4,643,178 A    2/1987  Nastari et al.
(Continued)

FOREIGN PATENT DOCUMENTS

EP    0322334 A1    6/1989
FR    2681525 A1    3/1993
(Continued)

OTHER PUBLICATIONS

Al Baz et al., "Modified Technique of Tension Band Wiring in Flexion Injuries of the Middle and Lower Cervical Spine," Spine, vol. 20, No. 11, 1995, p. 1241-1244.
(Continued)

*Primary Examiner* — Pedro Philogene
(74) *Attorney, Agent, or Firm* — Wilson Sonsini Goodrich & Rosati

(57) ABSTRACT

A method for coupling a prosthesis to a spinal segment in a patient includes the steps of selecting first and second reference points disposed along the spinal segment and pre-operatively measuring a target distance. The target distance extends between the first and second reference points while the patient is in a preferred posture such as the standing position. A prosthesis is coupled to the spinal segment and the prosthesis is then intra-operatively adjusted in order to set the distance between the first and second reference points based on the target distance.

20 Claims, 33 Drawing Sheets

Related U.S. Application Data continuation of application No. 14/732,633, filed on Jun. 5, 2015, now abandoned, which is a continuation of application No. 13/031,039, filed on Feb. 28, 2011, now abandoned, which is a continuation of application No. PCT/US2009/055914, filed on Sep. 3, 2009.

(60) Provisional application No. 61/093,922, filed on Sep. 3, 2008.

(58) Field of Classification Search
CPC ............ A61B 17/7043; A61B 17/7064; A61B 17/7097; A61B 17/842; A61B 17/68; A61B 17/70; A61B 17/7025; A61B 17/7026; A61B 2017/00725; A61B 2017/00858; A61B 2017/00867; A61B 2017/00004; A61B 2017/00537; A61B 2017/564; A61F 2/08; A61F 2/44; A61F 2/442
USPC .................... 606/74, 77, 105, 908, 246–289; 623/17.11–17.16
See application file for complete search history.

(56) References Cited

U.S. PATENT DOCUMENTS

| | | | |
|---|---|---|---|
| 4,743,260 A | 5/1988 | Burton | |
| 4,955,885 A | 9/1990 | Meyers | |
| 4,966,600 A | 10/1990 | Songer et al. | |
| 5,011,484 A | 4/1991 | Breard | |
| 5,092,866 A | 3/1992 | Breard et al. | |
| 5,116,340 A | 5/1992 | Songer et al. | |
| 5,180,393 A | 1/1993 | Commarmond | |
| 5,282,863 A | 2/1994 | Burton | |
| 5,395,374 A | 3/1995 | Miller et al. | |
| 5,415,658 A | 5/1995 | Kilpela et al. | |
| 5,415,661 A | 5/1995 | Holmes | |
| 5,449,361 A | 9/1995 | Preissman | |
| 5,456,722 A | 10/1995 | McLeod et al. | |
| 5,462,542 A | 10/1995 | Alesi, Jr. | |
| 5,496,318 A | 3/1996 | Howland et al. | |
| 5,540,698 A | 7/1996 | Preissman | |
| 5,562,737 A | 10/1996 | Graf | |
| 5,609,634 A | 3/1997 | Voydeville | |
| 5,628,756 A | 5/1997 | Barker, Jr. et al. | |
| 5,645,599 A | 7/1997 | Samani | |
| 5,725,582 A | 3/1998 | Bevan et al. | |
| 5,902,305 A | 5/1999 | Beger et al. | |
| RE36,221 E | 6/1999 | Breard et al. | |
| 5,928,232 A | 7/1999 | Howland et al. | |
| 5,935,133 A | 8/1999 | Wagner et al. | |
| 5,964,769 A | 10/1999 | Wagner et al. | |
| 5,989,256 A | 11/1999 | Kuslich et al. | |
| 6,053,921 A | 4/2000 | Wagner et al. | |
| 6,248,106 B1 | 6/2001 | Ferree | |
| 6,312,431 B1 | 11/2001 | Asfora | |
| 6,364,883 B1 | 4/2002 | Santilli | |
| 6,378,289 B1 | 4/2002 | Trudeau et al. | |
| 6,391,030 B1 | 5/2002 | Wagner et al. | |
| 6,436,099 B1 | 8/2002 | Drewry et al. | |
| 6,451,019 B1 | 9/2002 | Zucherman et al. | |
| 6,468,309 B1 | 10/2002 | Lieberman | |
| 6,582,433 B2 | 6/2003 | Yun | |
| 6,605,091 B1 | 8/2003 | Iwanski | |
| 6,626,944 B1 | 9/2003 | Taylor | |
| 6,629,975 B1 | 10/2003 | Kilpela et al. | |
| 6,652,527 B2 | 11/2003 | Zucherman et al. | |
| 6,652,585 B2 | 11/2003 | Lange | |
| 6,656,185 B2 | 12/2003 | Gleason et al. | |
| 6,669,729 B2 | 12/2003 | Chin | |
| 6,682,533 B1 | 1/2004 | Dinsdale et al. | |
| 6,689,140 B2 | 2/2004 | Cohen | |
| 6,689,168 B2 | 2/2004 | Lieberman | |
| 6,695,852 B2 | 2/2004 | Gleason | |
| 6,712,819 B2 | 3/2004 | Zucherman et al. | |
| 6,716,245 B2 | 4/2004 | Pasquet et al. | |
| 6,761,720 B1 | 7/2004 | Senegas | |
| 6,835,205 B2 * | 12/2004 | Atkinson ............... | A61B 17/70 623/17.11 |
| 7,029,475 B2 | 4/2006 | Panjabi | |
| 7,163,558 B2 | 1/2007 | Senegas et al. | |
| 7,458,981 B2 * | 12/2008 | Fielding ............. | A61B 17/7062 606/279 |
| 7,758,619 B2 | 7/2010 | Zucherman et al. | |
| 8,114,135 B2 | 2/2012 | Malandain | |
| 8,187,305 B2 | 5/2012 | Malandain et al. | |
| 8,308,771 B2 | 11/2012 | Bennett et al. | |
| 8,394,128 B2 | 3/2013 | Kothari et al. | |
| 8,403,961 B2 | 3/2013 | Fielding et al. | |
| 8,668,719 B2 * | 3/2014 | Alamin ............... | A61B 17/7064 606/248 |
| 10,092,331 B2 * | 10/2018 | Alamin ............... | A61B 17/7062 |
| 2002/0095154 A1 | 7/2002 | Atkinson et al. | |
| 2002/0099377 A1 | 7/2002 | Zucherman et al. | |
| 2002/0147449 A1 | 10/2002 | Yun | |
| 2002/0151978 A1 | 10/2002 | Zacouto et al. | |
| 2004/0024458 A1 | 2/2004 | Senegas et al. | |
| 2004/0106995 A1 | 6/2004 | Le Couedic et al. | |
| 2004/0116927 A1 | 6/2004 | Graf | |
| 2004/0117017 A1 | 6/2004 | Pasquet et al. | |
| 2004/0127989 A1 | 7/2004 | Dooris et al. | |
| 2004/0158245 A1 | 8/2004 | Chin | |
| 2004/0172132 A1 | 9/2004 | Ginn | |
| 2004/0243239 A1 | 12/2004 | Taylor | |
| 2005/0010220 A1 | 1/2005 | Casutt et al. | |
| 2005/0033435 A1 | 2/2005 | Belliard et al. | |
| 2005/0049708 A1 | 3/2005 | Atkinson et al. | |
| 2005/0123581 A1 | 6/2005 | Ringeisen et al. | |
| 2005/0131545 A1 | 6/2005 | Chervitz et al. | |
| 2005/0171543 A1 | 8/2005 | Timm et al. | |
| 2005/0216017 A1 | 9/2005 | Fielding et al. | |
| 2005/0267470 A1 | 12/2005 | McBride | |
| 2006/0069447 A1 | 3/2006 | DiSilvestro et al. | |
| 2006/0136060 A1 | 6/2006 | Taylor | |
| 2006/0167454 A1 | 7/2006 | Ludwig et al. | |
| 2006/0240533 A1 | 10/2006 | Sengupta et al. | |
| 2007/0043361 A1 | 2/2007 | Malandain et al. | |
| 2007/0213829 A1 | 9/2007 | Le Couedic et al. | |
| 2007/0233096 A1 | 10/2007 | Garcia-Bengochea | |
| 2008/0009863 A1 | 1/2008 | Bond et al. | |
| 2008/0009866 A1 | 1/2008 | Alamin et al. | |
| 2008/0108993 A1 | 5/2008 | Bennett et al. | |
| 2008/0262549 A1 | 10/2008 | Bennett et al. | |
| 2008/0319487 A1 | 12/2008 | Fielding et al. | |
| 2010/0234890 A1 | 9/2010 | Alamin et al. | |
| 2011/0172708 A1 | 7/2011 | Fielding et al. | |
| 2012/0059419 A1 | 3/2012 | Alamin et al. | |
| 2013/0012995 A1 | 1/2013 | Butterfield et al. | |
| 2016/0143670 A1 | 5/2016 | Todd et al. | |

FOREIGN PATENT DOCUMENTS

| | | |
|---|---|---|
| FR | 2775890 A1 | 9/1999 |
| GB | 2269753 A | 2/1994 |
| JP | 2007504895 A | 3/2007 |
| JP | 2008500085 A | 1/2008 |
| WO | WO-0128442 A1 | 4/2001 |
| WO | WO-0203882 A2 | 1/2002 |
| WO | WO-0203882 A3 | 5/2002 |
| WO | WO-02051326 A1 | 7/2002 |
| WO | WO-02071960 A1 | 9/2002 |
| WO | WO-03045262 A2 | 6/2003 |
| WO | WO-03045262 A3 | 1/2004 |
| WO | WO-2004052246 A1 | 6/2004 |
| WO | WO-2004073532 A1 | 9/2004 |
| WO | WO-2008051423 A1 | 5/2008 |
| WO | WO-2008051801 A2 | 5/2008 |
| WO | WO-2008051802 A2 | 5/2008 |
| WO | WO-2008051806 A2 | 5/2008 |
| WO | WO-2008051802 A3 | 7/2008 |
| WO | WO-2008051806 A3 | 7/2008 |
| WO | WO-2008051801 A3 | 8/2008 |
| WO | WO-2009149414 A1 | 12/2009 |

(56) References Cited

FOREIGN PATENT DOCUMENTS

OTHER PUBLICATIONS

Dickman et al., "Comparative Mechanical Properties of Spinal Cable and Wire Fixation Systems," Spine, vol. 22, No. 6, Mar. 15, 1997, pp. 596-604.

European search report dated Dec. 6, 2012 for EP Application No. 09812225.2.

Garner et al., "Development and Preclinical Testing of a New Tension-Band Device for the Spine: the Loop system," European Spine Journal, vol. 11 (Suppl 2), 2002, pp. S186-S191.

Heller, "Stability of Different Wiring Techniques in Segmental Spinal Instrumentation. An Experimental Study," Archives of Orthopedic and Trauma Surgery, vol. 117, No. 1-2, Nov. 1997, pp. 96-99.

International search report and written opinion dated Jan. 4, 2010 for PCT/US2009/055914.

Leahy et al., "Design of Spinous Process Hooks for Flexible Fixation of the Lumbar Spine," roceedings of the Institution of Mechanical Engineers, Part H, Journal of Engineering in Medicine, vol. 214, No. 5, Sep. 27, 2000, pp. 479-487.

Leahy et al., "Mechanical Testing of a Flexible Fixation Device for the Lumbar Spine," Proceedings of the Institution of Mechanical Engineers, Part H: Journal of Engineering in Medicine, vol. 214, No. 5, Sep. 27, 2000, pp. 489-495.

Minns et al., "Preliminary Design and Experimental Studies of a Novel Soft Implant for Correcting Sagittal Plane Instability in the Lumbar Spine," Spine, vol. 22, No. 16, Aug. 15, 1997, pp. 1819-1825.

Miyasaka et al., "Radiographic Analysis of Lumbar Motion in Relation to Lumbosacral Stability: Investigation of Moderate and Maximum Motion," Spine, vol. 25, No. 6, Mar. 15, 2000, pp. 732-737.

"Nadachair Website. Accessed Sep. 1, 2015.".

Office action dated May 9, 2014 for U.S. Appl. No. 13/037,039.

Office action dated Dec. 19, 2014 for U.S. Appl. No. 13/037,039.

Papp et al., "An In Vitro Study of the Biomechanical Effects of Flexible Stabilization on the Lumbar Spine," Spine, vol. 22, No. 2, Jan. 15, 1997, pp. 151-155.

Shepherd et al., "Spinous Process Strength," Spine, vol. 25, No. 3, Feb. 1, 2000, pp. 319-323.

Shepherd, "Slippage of a Spinous Process Hook During Flexion in a Flexible Fixation System for the Lumbar Spine," Medical Engineering and Physics, vol. 23, No. 2, Mar. 2001, pp. 135-141.

Voydeville, et al. Ligament intevertebral spacer with flexible lumbar instability. Ligamentoplastie intervertebrate avec cale souple dans les instabilities lombaries. Intervertebral ligamentoplasty with flexible wedge in lumber instability. Orthop Traumatol. 1992; 2:259-264. (in French with English translation).

* cited by examiner

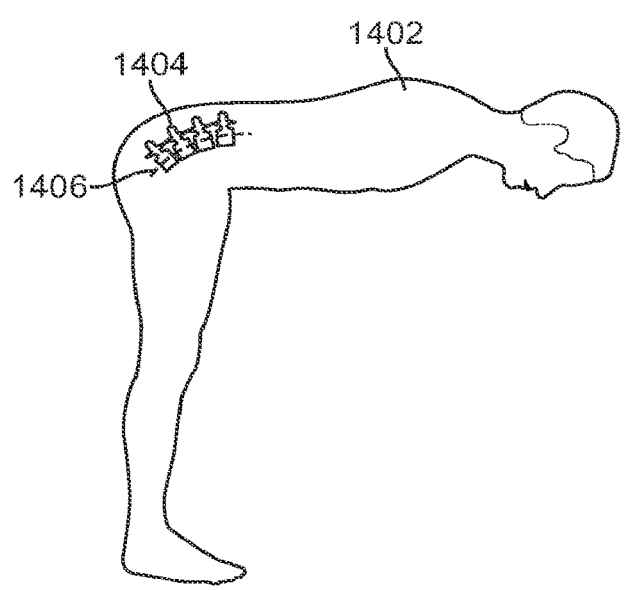
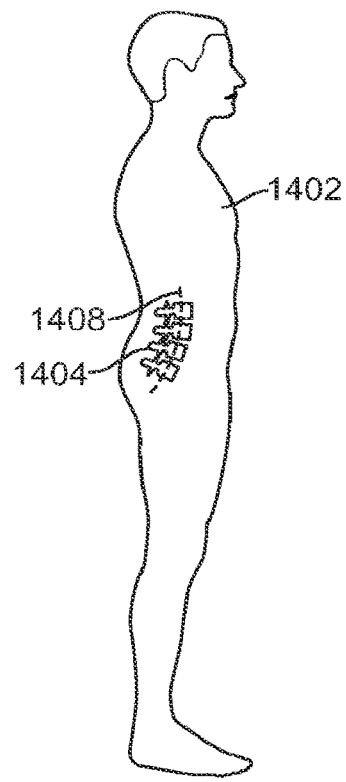
FIG. 14A
FIG. 14B
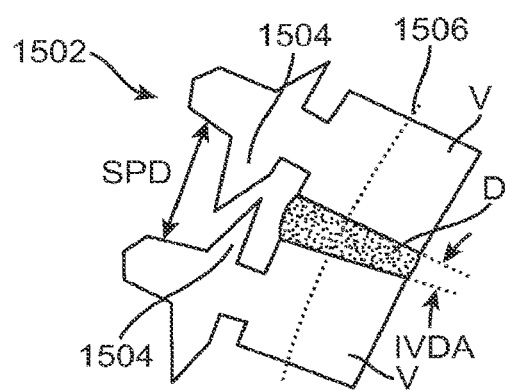
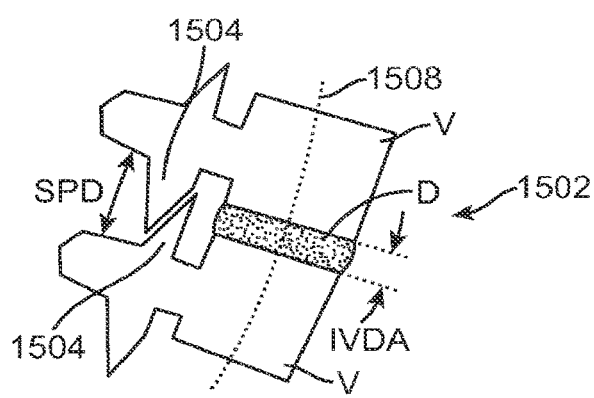
FIG. 15A
FIG. 15B

METHODS AND APPARATUS FOR COUPLING A PROSTHESIS TO A SPINAL SEGMENT

CROSS-REFERENCES TO RELATED APPLICATIONS

The present application is a continuation of U.S. patent application Ser. No. 15/397,611 filed Jan. 3, 2017 which is a continuation of U.S. patent application Ser. No. 14/732,633 filed Jun. 5, 2015 which is a continuation of U.S. patent application Ser. No. 13/037,039, filed Feb. 28, 2011, which is a continuation of International Patent Application No. PCT/US2009/055914, filed Sep. 3, 2009, which claims priority to U.S. Provisional Application No. 61/093,922, filed Sep. 3, 2008, the full disclosures of which are incorporated herein by reference.

BACKGROUND OF THE INVENTION

1. Field of the Invention

The present invention generally relates to medical methods and apparatus. More particularly, the present invention relates to methods and apparatus used to couple a prosthesis to a spinal segment and adjust the prosthesis during orthopedic internal fixation procedures. This includes but is not limited to treatment of patients having back pain or other spinal conditions.

A major source of chronic low back pain is discogenic pain, also known as internal disc disruption. Patients suffering from discogenic pain tend to be young, otherwise healthy individuals who present with pain localized to the back. Discogenic pain usually occurs at the discs located at the L4-L5 or L5-S1 junctions of the spine. Pain tends to be exacerbated when patients put their lumbar spines into flexion (i.e. by sitting or bending forward) and relieved when they put their lumbar spines into extension (i.e. by standing or arching backwards). Flexion and extension are known to change the mechanical loading pattern of a lumbar segment. When the segment is in extension, the axial loads borne by the segment are shared by the disc and facet joints (approximately 30% of the load is borne by the facet joints). In flexion, the segmental load is borne almost entirely by the disc. Furthermore, the nucleus shifts posteriorly, changing the loads on the posterior portion of the annulus (which is innervated), likely causing its fibers to be subject to tension and shear forces. Segmental flexion, then, increases both the loads borne by the disc and causes them to be borne in a more painful way. Discogenic pain can be quite disabling, and for some patients, can dramatically affect their ability to work and otherwise enjoy their lives.

Pain experienced by patients with discogenic low back pain can be thought of as flexion instability, and is related to flexion instability manifested in other conditions. The most prevalent of these is spondylolisthesis, a spinal condition in which abnormal segmental translation is exacerbated by segmental flexion. The methods and devices described herein should as such also be useful for these other spinal disorders or treatments associated with segmental flexion, for which the prevention or control of spinal segmental flexion is desired. Another application for which the methods and devices described herein may be used is in conjunction with a spinal fusion, in order to restrict motion, promote healing, and relieve pain post-operatively. Alternatively, the methods and devices described should also be useful in conjunction with other treatments of the anterior column of the spine, including kyphoplasty, total disc replacement, nucleus augmentation and annular repair.

Patients with discogenic pain accommodate their syndrome by avoiding positions such as sitting, which cause their painful segment to go into flexion, preferring positions such as standing, which maintain their painful segment in extension. One approach to reducing discogenic pain involves the use of a lumbar support pillow often seen attached to office chairs. Biomechanically, the attempted effect of the ubiquitous lumbar support pillow is also to maintain the painful lumbar segment in the less painful extension position.

Current treatment alternatives for patients diagnosed with chronic discogenic pain are quite limited. Many patients follow a conservative treatment path, such as physical therapy, massage, anti-inflammatory and analgesic medications, muscle relaxants, and epidural steroid injections, but typically continue to suffer with a significant degree of pain. Other patients elect to undergo spinal fusion surgery, which commonly requires discectomy (removal of the disk) together with fusion of adjacent vertebra. Fusion may or may not also include instrumentation of the affected spinal segment including, for example, pedicle screws and stabilization rods. Fusion is not lightly recommended for discogenic pain because it is irreversible, costly, associated with high morbidity, and has questionable effectiveness. Despite its drawbacks, however, spinal fusion for discogenic pain remains common due to the lack of viable alternatives.

An alternative method, that is not commonly used in practice, but has been approved for use by the United States Food and Drug Administration (FDA), is the application of bone cerclage devices which can encircle the spinous processes or other vertebral elements and thereby create a restraint to motion. Physicians typically apply a tension or elongation to the devices that applies a constant and high force on the anatomy, thereby fixing the segment in one position and allowing effectively no motion. The lack of motion allowed after the application of such devices is thought useful to improve the likelihood of fusion performed concomitantly; if the fusion does not take, these devices will fail through breakage of the device or of the spinous process to which the device is attached. These devices are designed for static applications and are not designed to allow for dynamic elastic resistance to flexion across a range of motion. The purpose of bone cerclage devices and other techniques described above is to almost completely restrict measurable motion of the vertebral segment of interest. This loss of motion at a given segment gives rise to abnormal loading and motion at adjacent segments, which can lead eventually to adjacent segment morbidity.

An alternative solution that avoids some of the challenges associated with cerclage devices involves the use of an elastic structure, such as tether structures, coupled to the spinal segment. The elastic structure can relieve pain by increasing passive resistance to flexion while often allowing substantially unrestricted spinal extension. This mimics the mechanical effect of postural accommodations that patients already use to provide relief.

Spinal implants using tether structures are currently commercially available. One such implant couples adjacent vertebrae via their pedicles. This implant includes spacers, tethers and pedicle screws. To install the implant, selected portions of the disc and vertebrae bone are removed. Implants are then placed to couple two adjacent pedicles on each side of the spine. The pedicle screws secure the implants in place. The tether is clamped to the pedicle screws with set-screws, and limits the extension/flexion movements of the vertebrae of interest. Because significant tissue is removed and because of screw placement into the pedicles, the implant and accompanying surgical methods are highly invasive and the implant is often irreversibly implanted. There is also an accompanying significant chance of nerve root damage. Additionally, the tip of the set-screw clamps the tethers, and this may result in abrasion of the tethers along with generation of particulate wear debris.

Other implants employing tether structures couple adjacent vertebrae via their processes instead. These implants include a tether and a spacer. To install the implant, the supraspinous ligament is temporarily lifted and displaced. The interspinous ligament between the two adjacent vertebrae of interest is then permanently removed and the spacer is inserted in the interspinous interspace. The tether is then wrapped around the processes of the two adjacent vertebrae, through adjacent interspinous ligaments, and then mechanically secured in place by the spacer or also by a separate component fastened to the spacer. The supraspinous ligament is then restored back to its original position. Such implants and accompanying surgical methods are not without disadvantages. These implants may subject the spinous processes to frequent, high loads during everyday activities, sometimes causing the spinous processes to break or erode. Furthermore, the spacer may put a patient into segmental kyphosis, potentially leading to long-term clinical problems associated with lack of sagittal balance. The process of securing the tethers is often a very complicated maneuver for a surgeon to perform, making the surgery much more invasive. And, as previously mentioned, the removal of the interspinous ligament is permanent. As such, the application of the device is not reversible.

More recently, less invasive spinal implants have been introduced. Like the aforementioned implant, these spinal implants are placed over one or more pairs of spinous processes and provide an elastic restraint to the spreading apart of the spinous processes occurring during flexion. However, extension-limiting spacers are not used and interspinous ligaments are not permanently removed. As such, these implants are less invasive and may be reversibly implanted. The implants typically include a tether structure and a securing mechanism for the tether. The tether may be made from a flexible polymeric textile such as woven polyester (PET) or polyethylene (e.g. ultra high molecular weight polyethylene, UHMWPE); multi-strand cable, or other flexible structure. The tether is wrapped around the processes of adjacent vertebrae and then secured by the securing mechanism. The securing mechanism may involve the indexing of the tether and the strap, e.g., the tether and the securing mechanism includes discrete interfaces such as teeth, hooks, loops, etc. which interlock the two. Highly forceful clamping may also be used to press and interlock the tether with the securing mechanism. Many known implementations clamp a tether with the tip of a set-screw, or the threaded portion of a fastener. However, the mechanical forces placed on the spinal implant are unevenly distributed towards the specific portions of the tether and the securing mechanism which interface with each other. These portions are therefore typically more susceptible to abrasion, wear, or other damage, thus reducing the reliability of these spinal implants as a whole. Other known methods use a screw or bolt to draw other components together to generate a clamping force. Other locking methods include the use of a friction fit and are disclosed in greater detail below. While these methods may avoid the potentially damaging loads, the mechanical complexity of the assembly may be increased by introducing more subcomponents.

A key to proper implantation of many of the spinous process constraint devices described above is adjusting the tension or size of the device when wrapped around the spinous processes. If the band is not properly adjusted, it may be too loose and therefore may disengage from the anatomy, or it may not provide adequate resistance to flexion resulting in failure to alleviate the pain or instability. On the other hand, if the band is too tight or too small, the device may provide too much resistance to flexion and unnecessarily restrict the spinal segment's ability to bend, or effect higher than necessary loads to portions of the vertebrae or soft tissues. It is therefore imperative to properly adjust the size and/or tension of the spinous process device. The device ideally should have a predetermined and preferred configuration while the patient is in a preferred posture (e.g. the standing position) and the device should also provide a force resistive to flexion of the spinal segment while still allowing significantly unrestricted extension of the spinal segment. For the aforementioned reasons, it would be desirable to provide improved methods and apparatus for coupling a prosthesis to a spinal segment and adjusting the prosthesis, especially during orthopedic internal fixation procedures. In particular, such methods and apparatuses should be easy to perform and be minimally invasive.

2. Description of the Background Art

Patents and published applications of interest include: U.S. Pat. Nos. 3,648,691; 4,643,178; 4,743,260; 4,966,600; 5,011,494; 5,092,866; 5,116,340; 5,180,393; 5,282,863; 5,395,374; 5,415,658; 5,415,661; 5,449,361; 5,456,722; 5,462,542; 5,496,318; 5,540,698; 5,562,737; 5,609,634; 5,628,756; 5,645,599; 5,725,582; 5,902,305; Re. 36,221; 5,928,232; 5,935,133; 5,964,769; 5,989,256; 6,053,921; 6,248,106; 6,312,431; 6,364,883; 6,378,289; 6,391,030; 6,468,309; 6,436,099; 6,451,019; 6,582,433; 6,605,091; 6,626,944; 6,629,975; 6,652,527; 6,652,585; 6,656,185; 6,669,729; 6,682,533; 6,689,140; 6,712,819; 6,689,168; 6,695,852; 6,716,245; 6,761,720; 6,835,205; 7,029,475; 7,163,558; Published U.S. Patent Application Nos. US 2002/0151978; US 2004/0024458; US 2004/0106995; US 2004/0116927; US 2004/0117017; US 2004/0127989; US 2004/0172132; US 2004/0243239; US 2005/0033435; US 2005/0049708; 2005/0192581; 2005/0216017; US 2006/0069447; US 2006/0136060; US 2006/0240533; US 2007/0213829; US 2007/0233096; 2008/0009866; 2008/0108993; Published PCT Application Nos. WO 01/28442 A1; WO 02/03882 A2; WO 02/051326 A1; WO 02/071960 A1; WO 03/045262 A1; WO2004/052246 A1; WO 2004/073532 A1; WO2008/051806; WO2008/051423; WO2008/051801; WO2008/051802; and Published Foreign Application Nos. EP0322334 A1; and FR 2 681 525 A1. The mechanical properties of flexible constraints applied to spinal segments are described in Papp et al. (1997) Spine 22:151-155; Dickman et al. (1997) Spine 22:596-604; and Garner et al. (2002) Eur. Spine J. S186-S191; Al Baz et al. (1995) Spine 20, No. 11, 1241-1244; Heller, (1997) Arch. Orthopedic and Trauma Surgery, 117, No. 1-2:96-99; Leahy et al. (2000) Proc. Inst. Mech. Eng. Part H: J. Eng. Med. 214, No. 5: 489-495; Minns et al., (1997) Spine 22 No. 16:1819-1825; Miyasaka et al. (2000) Spine 25, No. 6: 732-737; Shepherd et al. (2000) Spine 25, No. 3: 319-323; Shepherd (2001) Medical Eng. Phys. 23, No. 2: 135-141; and Voydeville et al (1992) Orthop Traumatol 2:259-264.

BRIEF SUMMARY OF THE INVENTION

The present invention relates to methods and apparatus used to couple a prosthesis to a spinal segment and adjust the prosthesis during orthopedic internal fixation procedures. This includes but is not limited to treatment of patients having spinal pain or other spinal conditions.

In a first aspect of the present invention, a method for coupling a prosthesis to a spinal segment in a patient comprises selecting a first and a second reference point disposed along the spinal segment and pre-operatively measuring a target distance. The target distance extends between the first and the second reference points while the patient is in a preferred posture. The method also includes coupling the prosthesis to the spinal segment and intra-operatively adjusting the prosthesis in order to set the distance between the first and second reference points based on the target distance.

The first reference point may be disposed on a first vertebra and the second reference point may be disposed on a second vertebra or a sacrum. The first reference point also may be disposed on a superior surface of a first spinous process of a first vertebra and the second reference point may be disposed on an inferior surface of a second spinous process of a second vertebra. The first reference point may also be disposed on an inferior surface of a first spinous process of a first vertebra and the second reference point may be disposed on a superior surface of a second spinous process of a second vertebra. The first vertebra may be disposed cranial to the second vertebra. The preferred posture may comprise the standing position or a pain-free position.

The measuring of the target distance may comprise observing a radiograph of the patient taken while the patient is in the preferred posture. The radiograph may be taken pre-operatively and may comprise a lateral view of the spinal segment. The prosthesis may comprise a tether structure and the coupling may comprise engaging a first portion of the tether structure with a superior spinous process and engaging a second portion of the tether structure with an inferior spinous process or a sacrum.

The adjusting may comprise adjusting the prosthesis so that the prosthesis is in a neutral position when the patient is in the preferred posture and the prosthesis may provide a force resistive to flexion of the spinal segment while still allowing significantly unrestricted extension of the spinal segment. The adjusting may also comprise adjusting the prosthesis while the patient is in a position other than the preferred posture or observing calibration markings on the prosthesis. Adjusting may also comprise setting the distance between the first and second reference points to the target distance.

The method may further comprise verifying that the distance between the first and second reference points substantially matches the target distance. Verifying may comprise using a gauge to determine the distance between the first and second reference points. The method may also comprise re-adjusting the prosthesis until the distance between the first and second reference points substantially matches the target distance.

The prosthesis may comprise a first compliance element and the method may further comprise engaging and locking a first constraining apparatus with the first compliance element in order to limit extension or contraction thereof during adjustment of the prosthesis. The first constraining apparatus may be disengaged from the first compliance element so as to allow movement thereof. The prosthesis may also comprise a second compliance element and the method may comprise engaging a second constraining apparatus with the second compliance element in order to limit extension or contraction thereof during adjustment of the prosthesis. The first and second constraining apparatus may be coupled so as to facilitate alignment and positioning of the first and the second compliance elements on opposite sides of a midline of the spinal segment. The first constraining apparatus may be moved relative to the second constraining apparatus along one degree of freedom in order to accommodate spinous processes or mid-line ligaments (e.g. interspinous ligament and superspinous ligament) of varying thicknesses. A driver or tool may be positioned in a central lumen of first or the second constraining apparatus thereby concentrically aligning the driver or the tool with a locking mechanism on the compliance element. The constraining apparatus may be used to provide a counter torque when the first or the second compliance elements are adjusted or when the first and the second constraining apparatus are releasably coupled together. The prosthesis may be pre-tensioned to a desired value.

The target distance may define a major axis length, and wherein the adjusting comprises using the target distance to determine a target prosthesis circumference, and adjusting the prosthesis to the target circumference. The major axis length may be correlated with the target circumference in a lookup table or with calibration markings on the prosthesis. The method may also include verifying that the prosthesis circumference substantially matches the target circumference. Verifying the prosthesis circumference may comprise observing calibration markings on the prosthesis. The prosthesis may be re-adjusted until the prosthesis circumference substantially matches the target circumference.

The method may also comprise selecting a third and a fourth reference point disposed along the spinal segment. The distance between the third and fourth reference points may define a minor axis having a minor axis length with the minor axis being transverse to the major axis. The method may also include measuring the minor axis length on the pre-operative image in order to determine the target prosthesis circumference. The target circumference may be sufficient for the prosthesis to form a loop encircling a superior spinous process and an inferior spinous process. The prosthesis may provide a force resistant to flexion beyond a desired posture. The third and fourth reference points may be on opposite sides of a spinous process and may be used to estimate the length of the prosthesis required to accommodate spinous process width. The third and fourth reference points may be disposed on a single vertebra. The minor axis length may be correlated with the target circumference in a lookup table or the minor axis length may be correlated with calibration markings on the prosthesis. The method may further comprise decompressing a portion of the spinal segment.

In another aspect of the present invention, a system for restricting flexion of a spinal segment in a patient comprises a tether structure adapted to be coupled with a superior spinous process and an inferior spinous process or sacrum, and a first compliance element coupled with the tether structure. The system also includes a first constraining tool releasably coupled with the compliance element so as to hold the compliance element in a desired position or to limit motion of the compliance element to a predetermined range. The tether structure may be substantially non-distensible and the first constraining tool may comprise an elongate shaft. The first constraining tool may comprise a cradle adapted to releasably hold the first compliance element. The first constraining tool may also comprise a plurality of elongate arms that form a receptacle for releasably holding the first compliance element and that constrain elongation of the compliance element. The first tool may hold the first compliance element in a desired tension or apply a compressive force to the first compliance element. The compressive force may be variable.

The first constraining tool may not limit extension of the first compliance element until the first compliance element has extended a pre-determined distance. The first constraining tool may be adjustable so as to vary the desired position, tension or the range. The system may also include a second compliance element coupled with the tether structure and a second constraining tool. The second tool may be releasably coupled with the second compliance element so as to hold the second compliance element in a desired position or to limit motion of the second compliance element to a predetermined range. The first and the second constraining tools may be releasably and symmetrically coupled together so as to facilitate alignment and positioning of the first and the second compliance elements on opposite sides of a midline of the spinal segment. The first and the second constraining tools may be movable relative to one another along one degree of freedom, thereby accommodating spinous processes or midline soft tissues of varying thicknesses. The first or the second compliance element may comprise a locking mechanism and at least one of the first or the second constraining tools may comprise an elongate shaft having a lumen adapted to receive and align a driver or other tool concentrically with the locking mechanism. The first or the second compliance element releasably locks with the first or the second constraining tool. The first or the second tool may also be adapted to provide to provide a counter torque when the locking mechanism is actuated.

In another aspect of the present invention, a method for treating lower back pain in a patient comprises providing instructions to the patient to place the lower back into varying positions of flexion and determining a threshold position of the lower back in which the patient does not experience lower back pain or where lower back pain is reduced. A first image or a set of images of the patient's lower back in the threshold position is provided and features of the patient's lower back are measured using the first image or the set of images. A constraint device is coupled to the patient's lower back and features of the lower back are re-measured with the constraint device coupled thereto. The re-measured features are compared with the measured features and the constraint device is adjusted so that the patient's lower back is in a position below the threshold position based on the comparison of measured and re-measured features. Thus, the lower back pain or lower back instability is reduced or eliminated.

The step of determining may comprise providing the patient with means for indicating when pain is experienced. The means may comprise an actuatable switch. The first image or the set of images may comprise one of an x-ray, MRI, and a CT scan. The providing step may comprise acquiring the set of images from a single continuous movement of the patient's lower back between painful and pain-free or reduced pain postures.

The measured features may comprise one of intervertebral disc angle, interspinous process distance, and interpedicular distance. The measuring may comprise using calipers or an angle measuring device to quantify the features.

The step of coupling may comprise engaging the constraint device with a superior spinous process and an inferior spinous process or a sacrum. The constraint device may be adapted to provide a force resistant to flexion of the lower back.

The step of re-measuring may comprise providing a second image or a set of images of the patient's lower back with the constraint device coupled thereto. The second image or the set of images may comprise one of an x-ray, MRI, and a CT scan. Re-measuring may comprise placing one or more radiopaque markers into engagement with the patient's lower back. The radiopaque markers may be coupled with a spinous process in the patient's lower back. The comparing step may comprise visually comparing the first and the second radiographic images or sets of images. Adjusting may comprise adjusting length or tension of the constraint device.

The method may further comprise evaluating presence and shape of spinous processes of the lower back for coupling of the constraint device thereto. Facet joint engagement in the lower back may also be evaluated. Evaluating may comprise measuring linear overlap of articular processes of the facet joint. Adjusting the constraint device may comprise adjusting the constraint device so as to increase facet joint engagement in at least one facet joint in the lower back. Adjusting may also comprise adjusting the constraint device so as to prevent hyperextension or locking of at least one facet joint in the lower back. The method may further comprise manipulating the patient's lower back intraoperatively so that the lower back is in a position at or below the threshold position based on the comparison of measured and re-measured features. The manipulating may comprising manipulating the patient's lower back to form or increase lordosis therein.

In another aspect of the present invention, a method for treating degenerative spondylolisthesis in a lower back of a patient comprises providing instructions to the patient to place the lower back into varying positions of flexion and providing a plurality of images of the lower back in the varying positions. A threshold position of the lower back in which a facet joint of the patient's lower back begins to sublux is determined, and a first image of the patient's lower back while in the threshold position is then provided. A constraint device is coupled to the patient's lower back, and a second image of the patient's back is provided intraoperatively after the constraint device has been coupled to the patient's lower back. The first and the second images are compared and the constraint device is adjusted so that the patient's lower back is in a position below the threshold position based on the comparison of the first and the second images. Thus, subluxation of the facet joint is reduced or eliminated.

The step of determining may comprise providing the patient with means for indicating when pain is experienced such as an actuatable switch. A neural decompression may be performed concurrently. The determining may also comprise assessing engagement of a facet joint or ability of the facet joint to resist anterior translation of the cranial vertebra with respect to the caudal vertebra.

The first image may comprise one of an x-ray, MRI, and CT scan. The coupling may comprise engaging the constraint device with a superior spinous process and an inferior spinous process or a sacrum. The constraint device may be adapted to provide a force resistant to flexion of the lower back. The second image may comprise an x-ray, MRI, or a CT scan. One or more radiopaque markers may be placed into engagement with the patient's lower back. The placement may comprise coupling a radiopaque marker with a spinous process in the patient's lower back.

The comparing step may comprise comparing intervertebral disc angle, interspinous process distance, facet joint engagement, or interpedicular distance between the first and the second images or sets of images. The comparing may also comprise using calipers or an angle measuring device to quantify lower back features in the first and the second images. The first and second images may be visually compared with one another.

The adjusting step may comprise adjusting length or tension of the constraint device. The method may also comprise evaluating presence and shape of spinous processes of the lower back for coupling of the constraint device thereto.

In another aspect of the present invention, a method for treating lower back pain in a patient comprises manipulating the patient's lower back into a position where the lower back pain is reduced or eliminated and recording the position. The position is intraoperatively reproduced in the patient's lower back and a constraint device is coupled to the lower back. The step of manipulating may comprise manually manipulating the patient's lower back, forming, or increasing lordosis in the patient's lower back. The manipulating may also comprise placing the patient in a frame or a chair with an adjustable lumbar member, or flexing a hip. The flexing of the hip may comprise directing a force proximally through a femoral head to antevert a pelvis thereby forming or increasing lordosis in the patient's lower back. The knee may be restrained.

The step of recording may comprise providing the patient with means for indicating when pain is experienced such as an actuatable switch. The step of reproducing may comprise manually manipulating the patient's lower back into the position or forming or increasing lordosis in the patient's lower back. The step of coupling may comprise engaging the constraint device with a superior spinous process and an inferior spinous process or a sacrum. The constraint device may be adapted to provide a force resistant to flexion of the lower back.

The method may further comprise providing an image of the patient's lower back in the position. The image may comprise an x-ray, MRI, or a CT scan. The method may also comprise providing an intraoperative image of the patient's lower back after reproducing the position. The intraoperative image may comprise one of an x-ray, C-arm fluoroscopy, MRI, or CT scan. A radiopaque marker may be coupled with the patient's lower back, such as with a spinous process. The method may further comprise intraoperatively characterizing range of motion, segmental stability, linear stiffness, or bending stiffness of a segment of the patient's lower back. The constraint device may be adjusted based on the characterization of the patient's lower back. The adjusting step may comprise adjusting length or tension in the constraint device. Additionally, the characterization of the patient's lower back may be compared with a reference guide and the constraint device may be adjusted based on information provided by the reference guide.

In still another aspect of the present invention, a method for treating spondylolisthesis in a patient comprises providing instructions to the patient to place the lower back into varying positions of flexion and determining a threshold position of the lower back in which the patient does not experience translational instability or wherein translation instability is reduced. A first image or a set of images of the patient's lower back is provided while the patient is in the threshold position and features of the patient's lower back are measured from the first image or the set of images. A constraint device is coupled to the patient's lower back and features of the patient's lower back are re-measured with the constraint device coupled thereto. The re-measured features are compared with the measured features, and the constraint device is adjusted so that the patient's lower back is in a position below the threshold position based on the comparison of measured and re-measured features, thereby reducing or eliminating the lower back instability.

These and other embodiments are described in further detail in the following description related to the appended drawing figures.

BRIEF DESCRIPTION OF THE DRAWINGS

FIGS. 14A-14B illustrate a patient in different postures.

FIGS. 15A-15B illustrate a spinal motion segment in kyphosis and lordosis.

DETAILED DESCRIPTION OF THE INVENTION

Figure 1A:
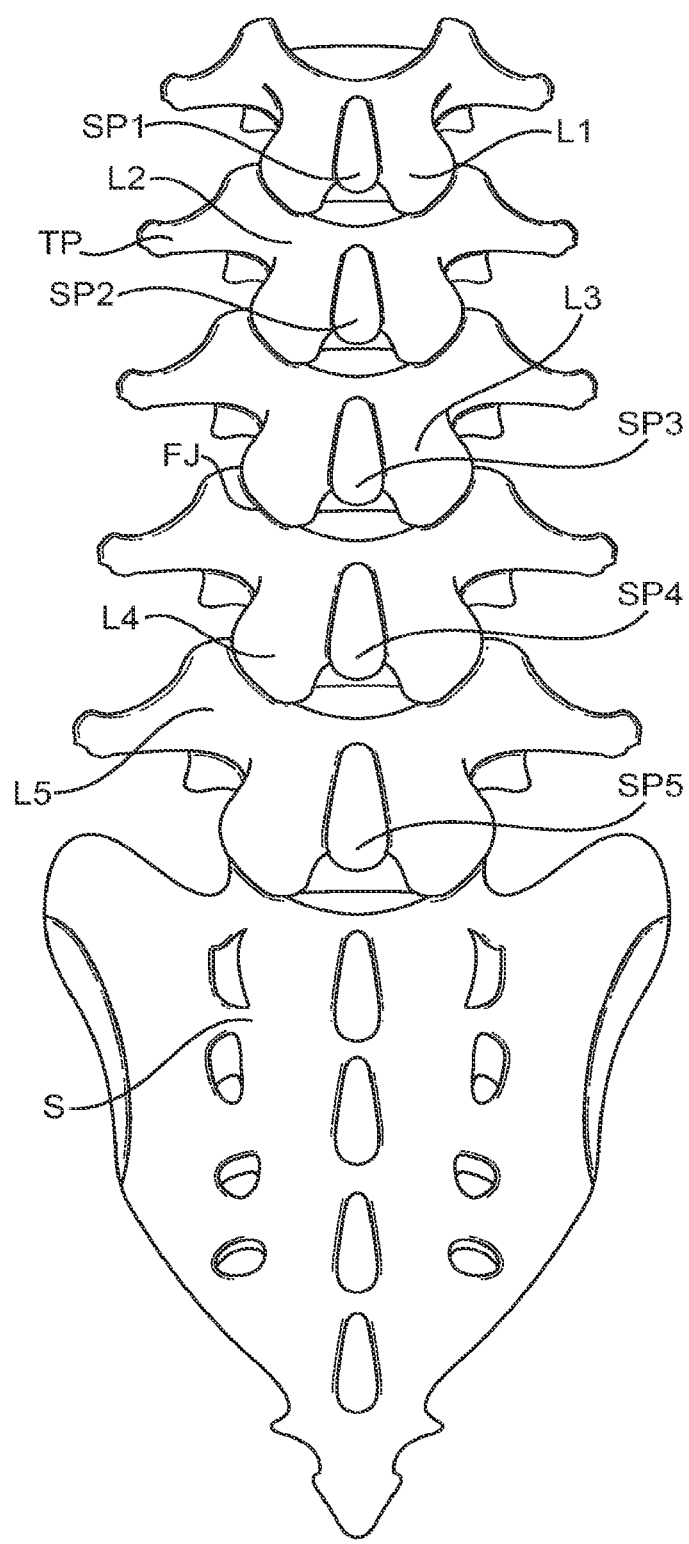
FIG. 1A is a schematic diagram illustrating the lumbar region of the spine.
Figure 1B:
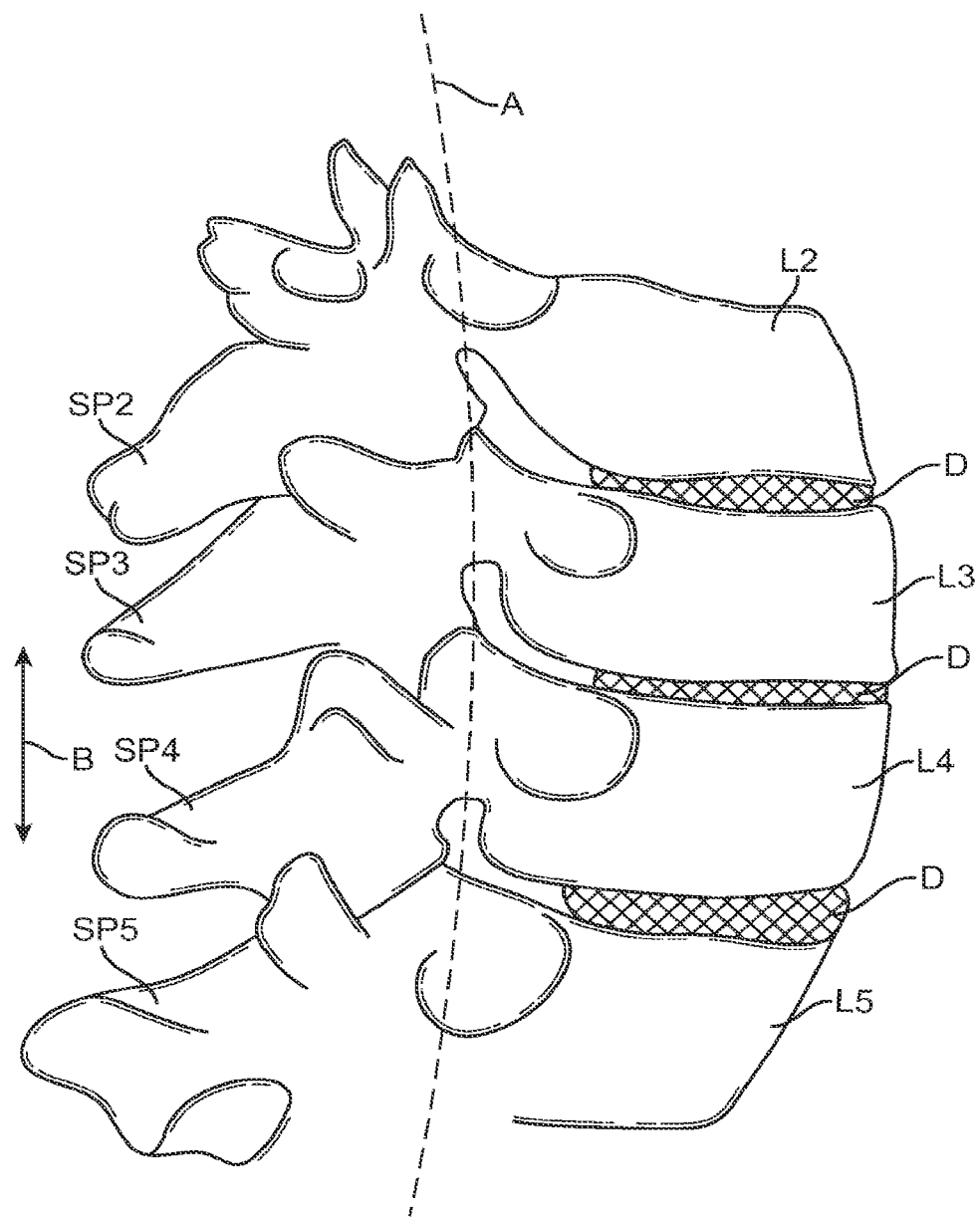
FIG. 1B a schematic illustration showing a portion of the lumbar region of the spine taken along a sagittal plane.

FIG. 1A is a schematic diagram illustrating the lumbar region of the spine including the spinous processes (SP), facet joints (FJ), lamina (L), transverse processes (TP), and sacrum (S). FIG. 1B is a schematic illustration showing a portion of the lumbar region of the spine taken along a sagittal plane and is useful for defining the terms "neutral position," "flexion," and "extension" that are often used in this disclosure.

As used herein, "neutral position" refers to the position in which the patient's spine rests in a relaxed standing position. The "neutral position" will vary from patient to patient. Usually, such a neutral position will be characterized by a slight curvature or lordosis of the lumbar spine where the spine has a slight anterior convexity and slight posterior concavity. In some cases, the presence of the constraint of the present invention may modify the neutral position, e.g. the device may apply an initial force which defines a "new" neutral position having some extension of the untreated spine. As such, the use of the term "neutral position" is to be taken in context of the presence or absence of the device. As used herein, "neutral position of the spinal segment" refers to the position of a spinal segment when the spine is in the neutral position.

Furthermore, as used herein, "flexion" refers to the motion between adjacent vertebrae in a spinal segment as the patient bends forward. Referring to FIG. 1B, as a patient bends forward from the neutral position of the spine, i.e. to the right relative to a curved axis A, the distance between individual vertebrae L on the anterior side decreases so that the anterior portion of the intervertebral disks D are compressed. In contrast, the individual spinous processes SP on the posterior side move apart in the direction indicated by arrow B. Flexion thus refers to the relative movement between adjacent vertebrae as the patient bends forward from the neutral position illustrated in FIG. 1B.

Additionally, as used herein, "extension" refers to the motion of the individual vertebrae L as the patient bends backward and the spine extends from the neutral position illustrated in FIG. 1B. As the patient bends backward, the anterior ends of the individual vertebrae will move apart. The individual spinous processes SP on adjacent vertebrae will move closer together in a direction opposite to that indicated by arrow B.

Figure 2:
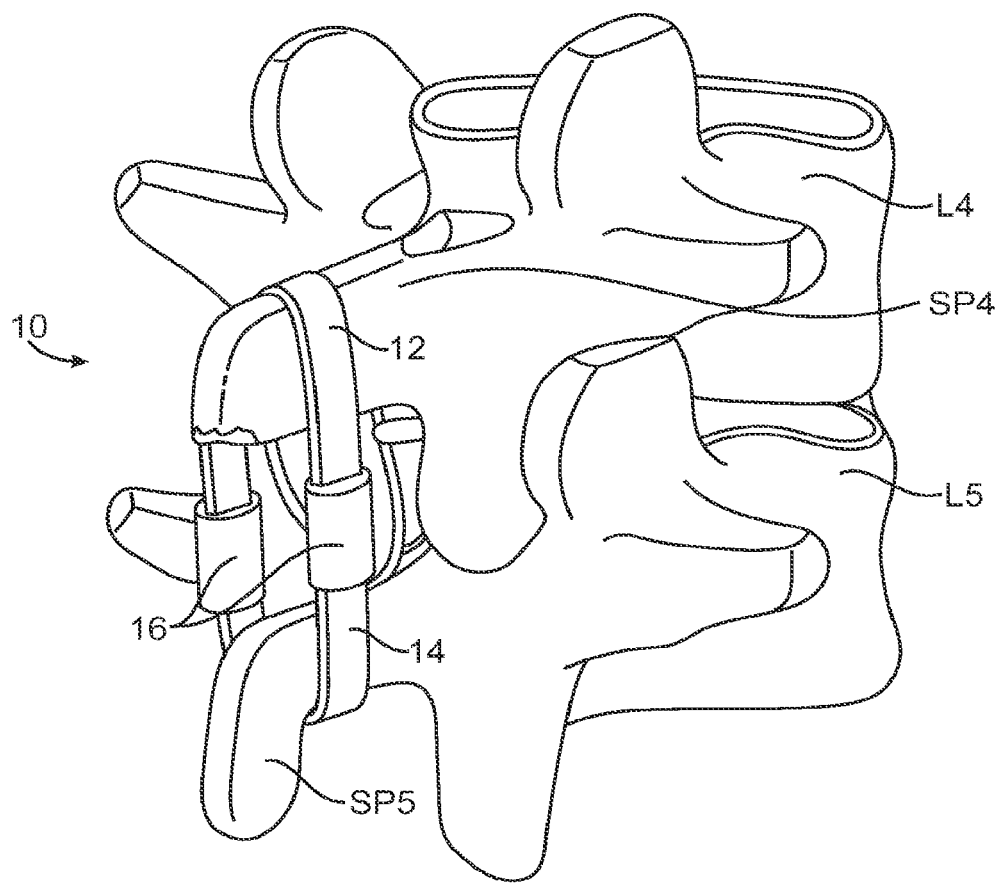
FIG. 2 illustrates a spinal implant of the type described in US 2005/0216017A1.

FIG. 2 shows a spinal implant of the type described in related U.S. Patent Publication No. 2005/02161017 A1, the entire contents of which are incorporated herein by reference. As illustrated in FIG. 2, an implant 10 typically comprises a tether structure having an upper strap component 12 and a lower strap component 14 joined by a pair of compliance elements 16. The upper strap 12 is shown disposed over the top of the spinous process SP4 of L4 while the lower strap 14 is shown extending over the bottom of the spinous process SP5 of L5. The compliance element 16 will typically include an internal element, such as a spring or rubber block, which is attached to the straps 12 and 14 in such a way that the straps may be "elastically" or "compliantly" pulled apart as the spinous processes SP4 and SP5 move apart during flexion. In this way, the implant provides an elastic tension on the spinous processes which provides a force that resists flexion. The force increases as the processes move further apart. Usually, the straps themselves will be essentially non-compliant so that the degree of elasticity or compliance may be controlled and provided solely by the compliance elements 16.

Figure 3A:
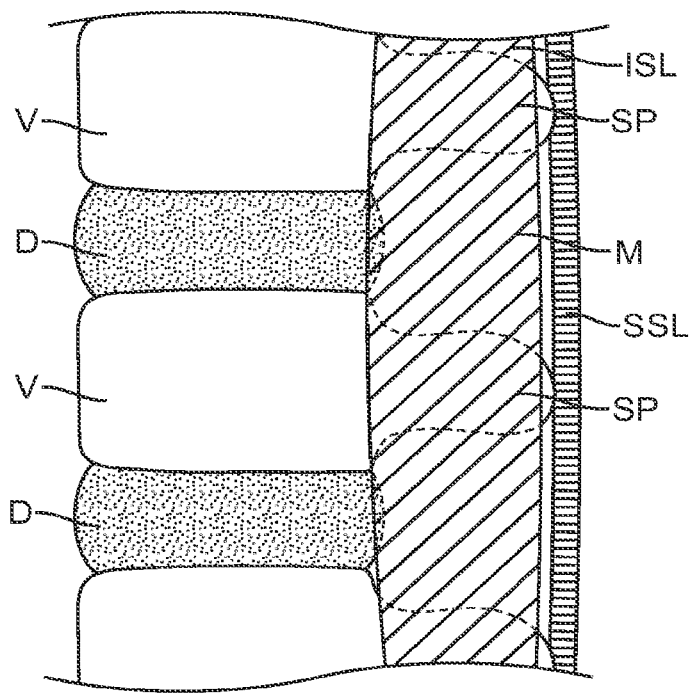
FIGS. 3A-3B illustrate additional tissue surrounding the spinous processes.
Figure 3B:
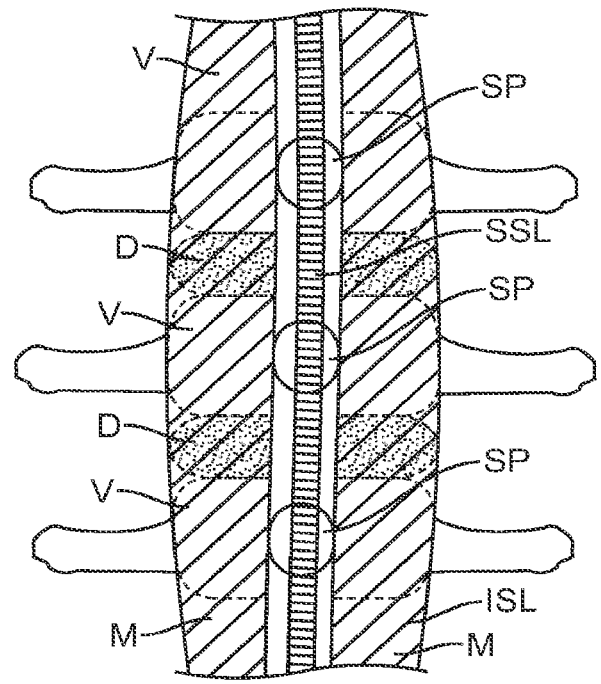

FIG. 3A is a side view of the lumbar region of the spine having discs D separating the vertebral bodies V. The supraspinous ligament SSL runs along the posterior portion of the spinous processes SP and the interspinous ligament ISL and multifidus tendon and muscle M run alongside of and attach to the spinous processes SP. FIG. 3B is a posterior view of FIG. 3A.

Figure 4A:
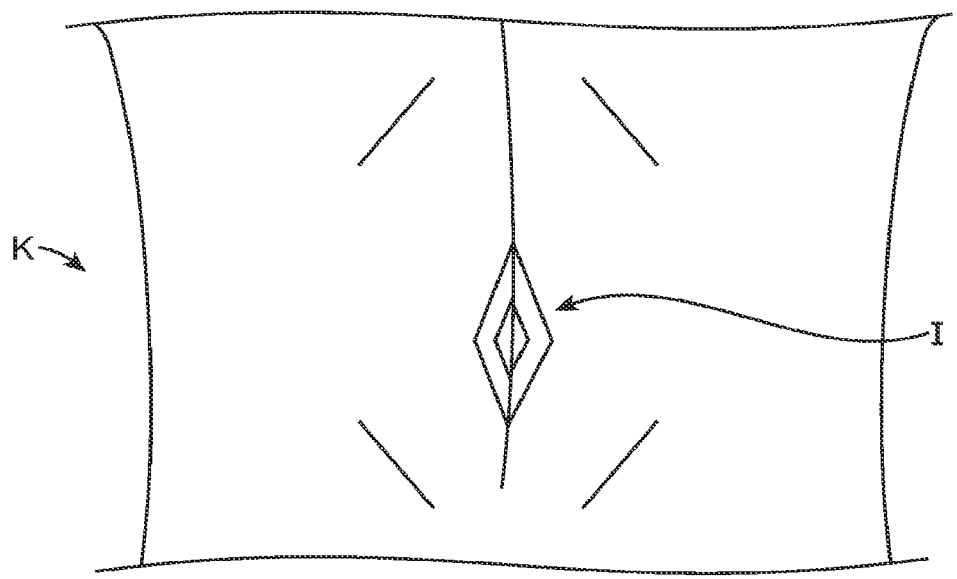
FIGS. 4A-4M show an exemplary method of surgically implanting a spinal device.
Figure 4B:
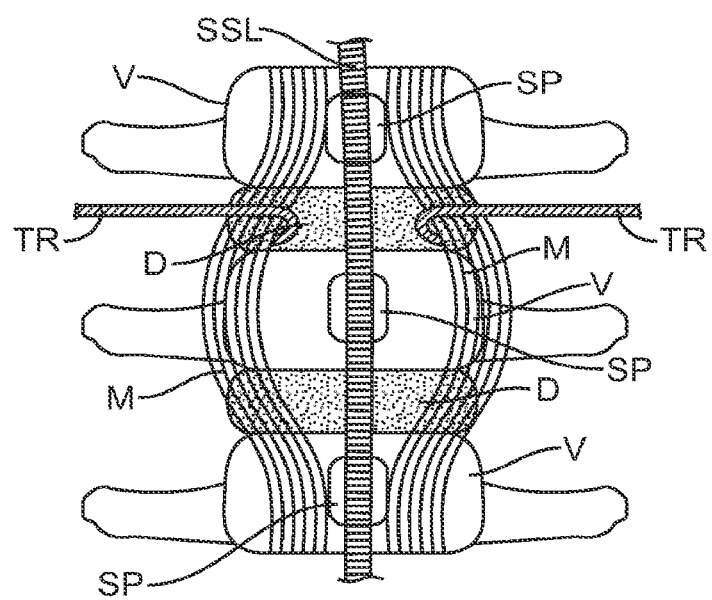

FIGS. 4A-4M illustrate an exemplary surgical method of implanting a spinous process constraint such as the embodiment of FIG. 2. One of the first steps to surgically implant a spinal implant is to make an incision to access the spinal area of interest. FIG. 4A shows the lumbar region of back K after an incision I has been made through the patient's skin. FIG. 4B illustrates the lumbar region of the spine after the incision I has been made through the patient's skin. Multifidus muscle and tendon M have been retracted with retraction tools TR to expose the spinous processes.

Figure 4D:
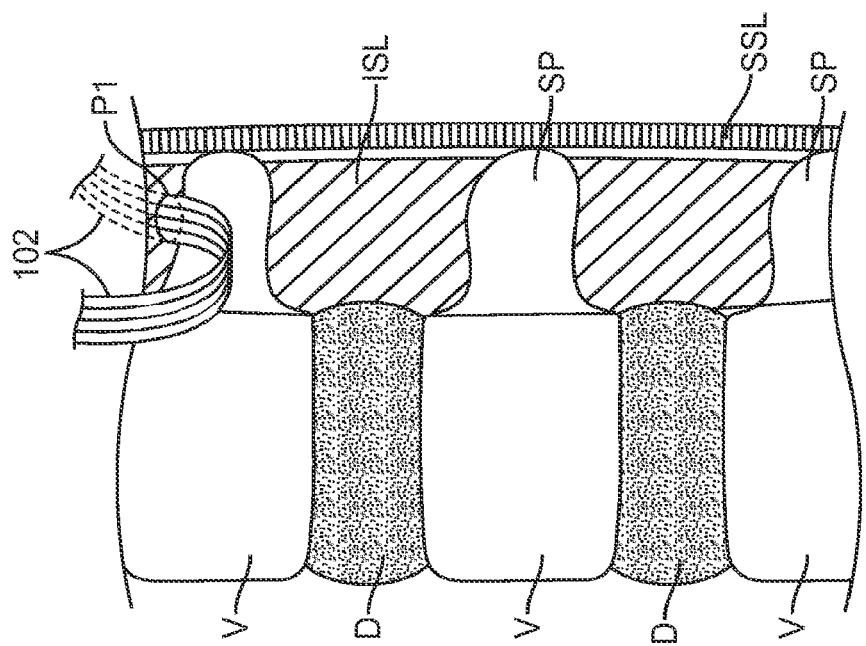
Figure 4C:
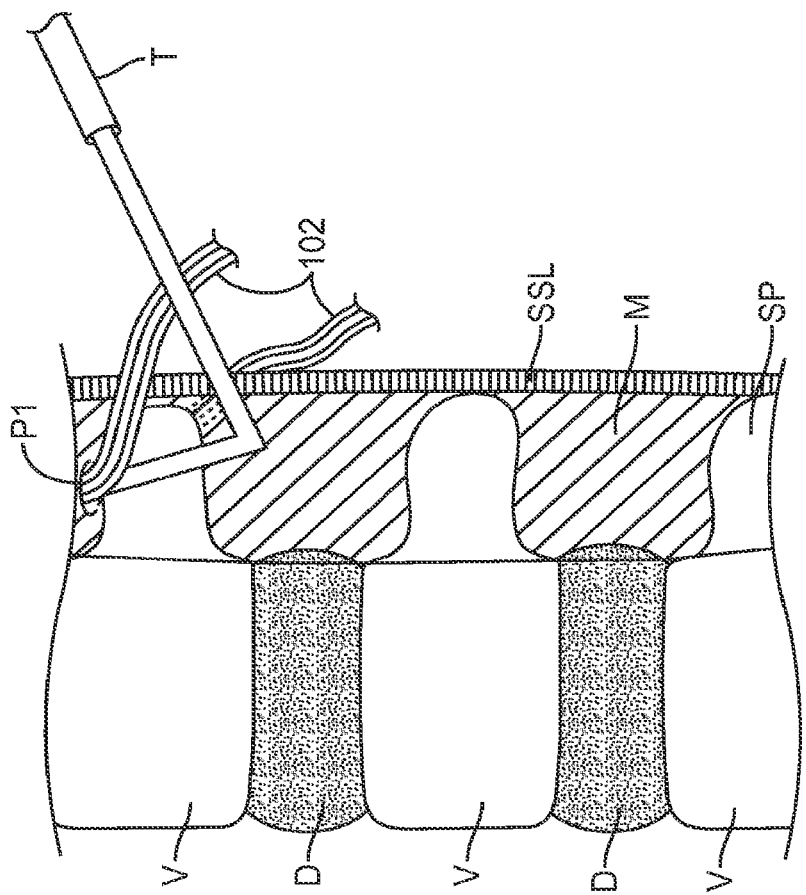

After the incision has been made, a piercing tool T having a tapered distal end may be used to access and pierce the interspinous ligament ISL while avoiding the supra spinous ligament SSL, creating an interspinous ligament perforation P1 superior of the first spinous process SSP of interest. Exemplary embodiments of piercing tool T are disclosed in U.S. patent application Ser. No. 12/478,953, the entire contents of which are incorporated herein by reference. This surgical approach is desirable since it keeps the supra spinous ligament intact and minimizes damage to the multifidus muscle and tendons and other collateral ligaments. As shown in FIG. 4C, from the right side of the spine, tool T accesses and pierces the interspinous ligament ISL adjacent of the first spinous process SSP of interest. The distal end of tool T is shown in dotted line. Alternatively, tool T may access and pierce the interspinous ligament ISL from the left side instead. The distal end of tool T is coupled with tether 102, parts of which are also shown in dotted line. In addition to accessing and piercing the interspinous ligament ISL, piercing tool T also advances or threads tether 102 through perforation P1. As shown in FIG. 4D, tool T is then removed, leaving tether 102 positioned through perforation P1. Multifidus tendon and muscle M is not shown in FIGS. 4C and 4D so that other elements are shown more clearly.

Figure 4E:
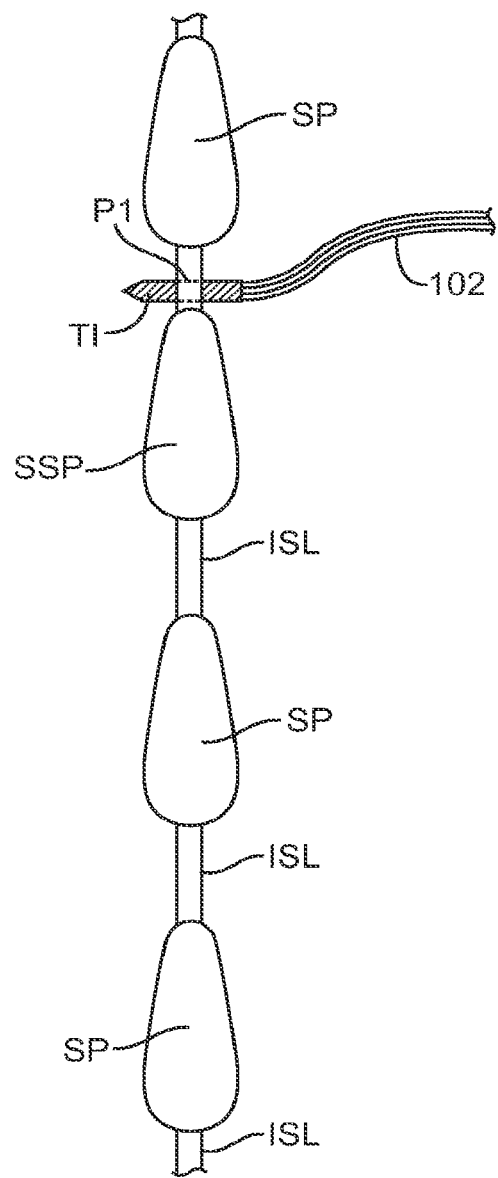

FIG. 4E is a posterior view of a section of the spine after the above steps have been performed. Often times, the distal tip TI of tool T is detachable. As shown in FIG. 4E, after tool T accesses and pierces the interspinous ligament ISL with distal tip TI, distal tip TI is detached from tool T and is left in place in perforation P1 (shown in dotted line) above the first spinous process SSP of interest. Tether 102 lags behind tip TI. In some cases, distal tip TI may fully pierce through interspinous ligament ISL. In these cases, distal tip TI has passed through the interspinous ligament ISL while a portion of tether 102 is left in place in perforation P1.

Figure 4F:
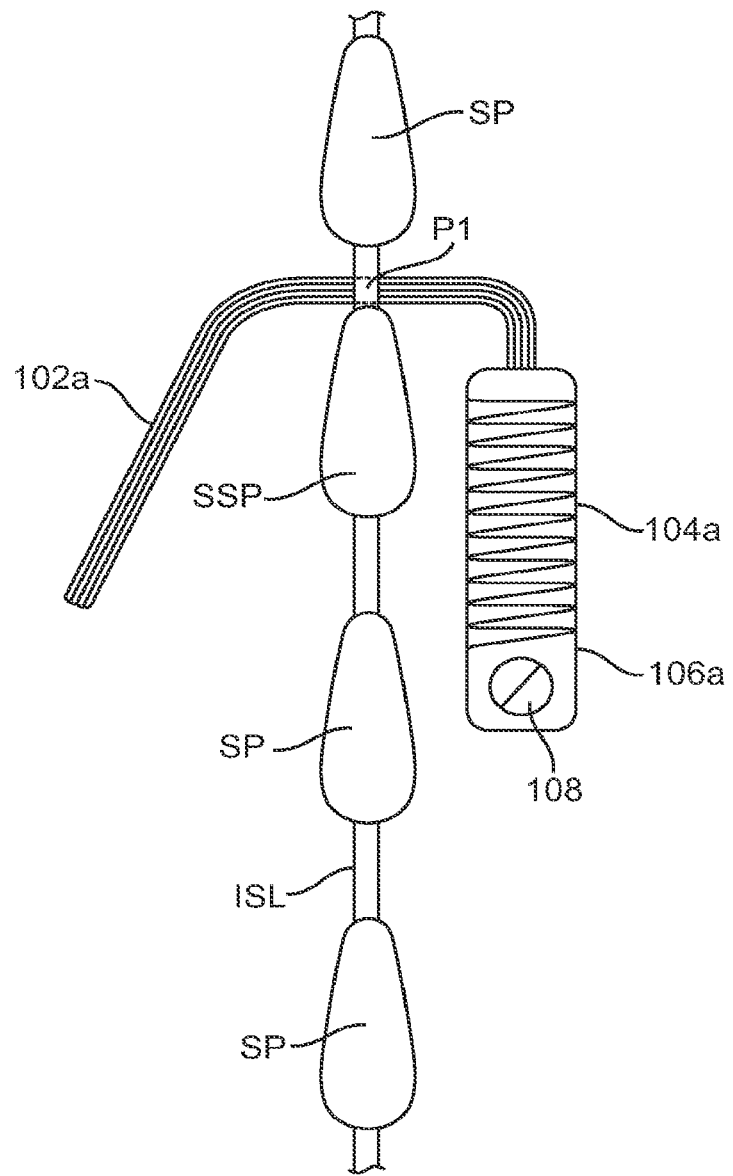

After tip TI or a portion of tether 102a is left in place in perforation P1, another tool may couple with tip TI and pull tip TI such that it drags tether 102a and compliance element 104a to its appropriate position relative to the spine, as shown in FIG. 4F. Compliance element 104a is coupled to tether 102a and is used to provide a force resistive to flexion of spinous processes SP. Compliance element 104a includes a fastening mechanism or fastening element 106a and may further comprise a spring, a tensioning member, a compression member, or the like. Related compliance elements are described in commonly owned U.S. patent application Ser. No. 12/106,103, the entire contents of which are incorporated herein by reference.

Figure 4H:
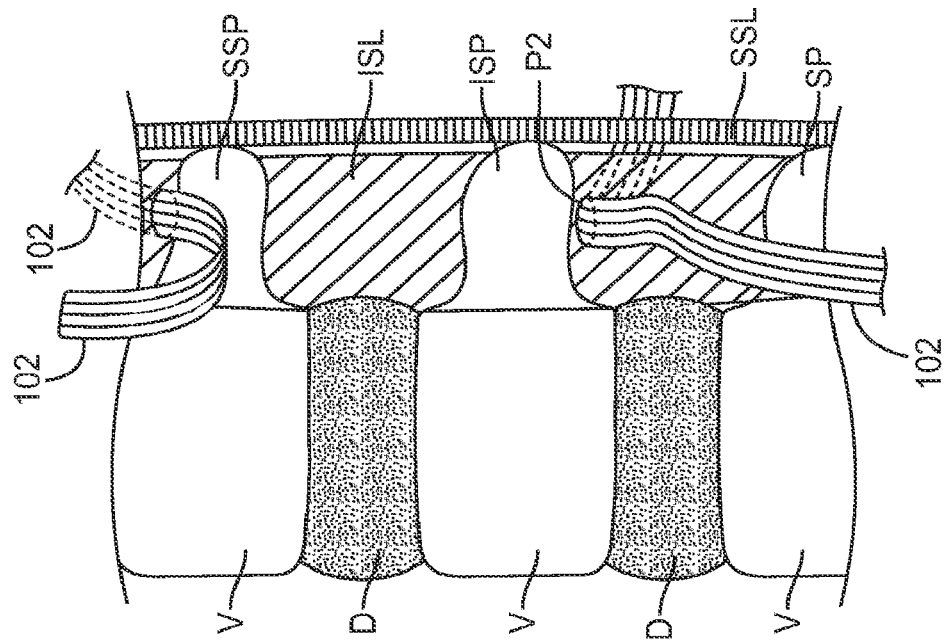
Figure 4G:
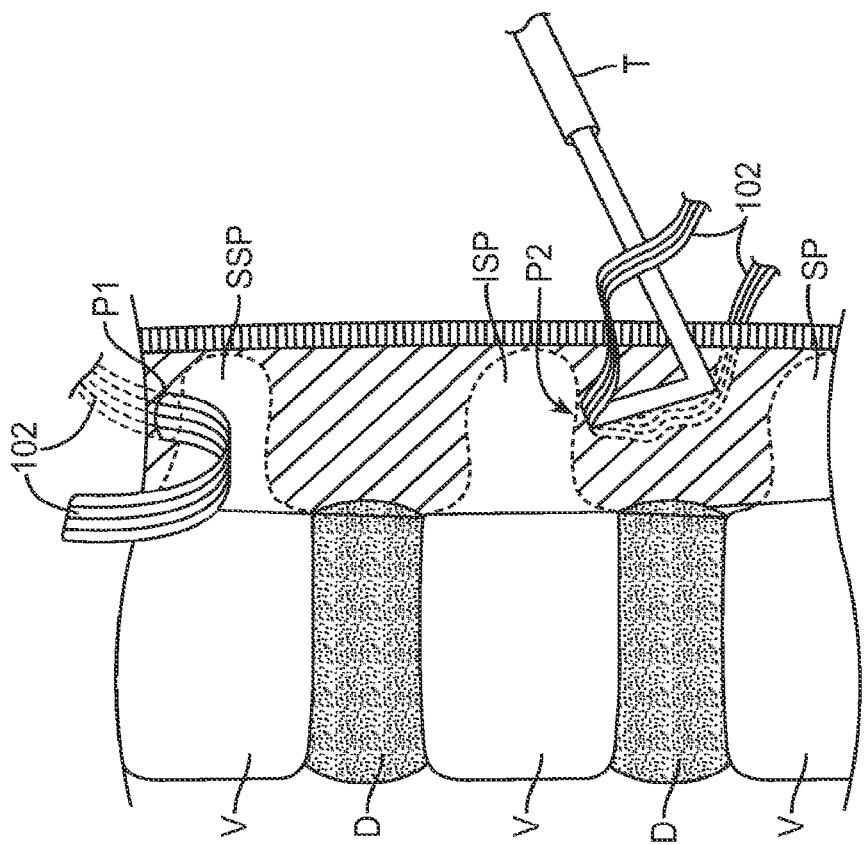

The steps of accessing the ISL, piercing the ISL, and threading tether 102 through a perforation are then repeated for the opposite, lateral side of the spine for an adjacent spinous process ISP, inferior of the first superior spinal process SSP of interest. As shown in FIGS. 4G and 4H, tool T accesses the interspinous ligament from the left side of the spinal midline and pierces the interspinous ligament ISL, creating a second perforation P2 located inferior of a second spinous process of interest, labeled as inferior spinous process ISP. One of skill in the art will appreciate that the piercing may also be performed from the opposite direction. As shown in FIG. 4G, the inferior spinous process ISP of interest is directly adjacent to and inferior of the first superior spinous process SSP of interest. However, it is entirely possible to perform the described procedure starting with the inferior spinous process ISP first instead of the superior spinous process SSP, for example, perforation P2 may be created before perforation P1. It is also possible that there may be a gap of one or more spinous processes SP between the spinous processes of interest. Multifidus tendon and muscle M is not shown in FIGS. 4G and 4H for clarity of the other shown elements.

Figure 4I:
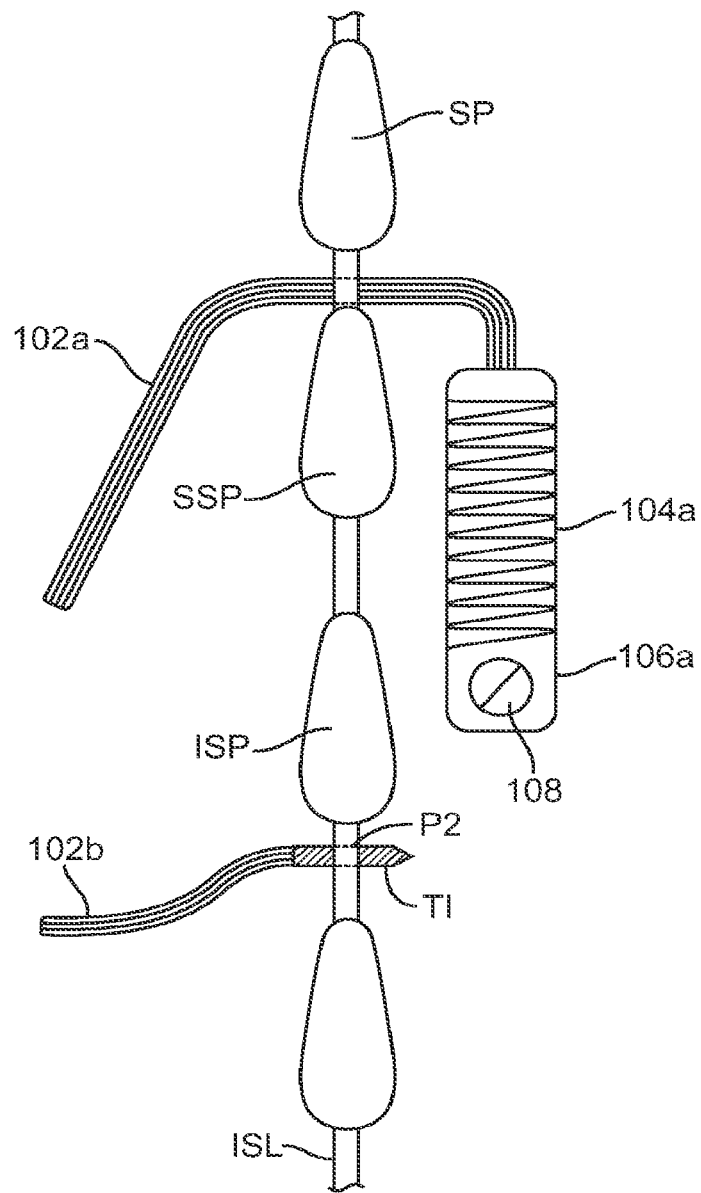
Figure 4J:
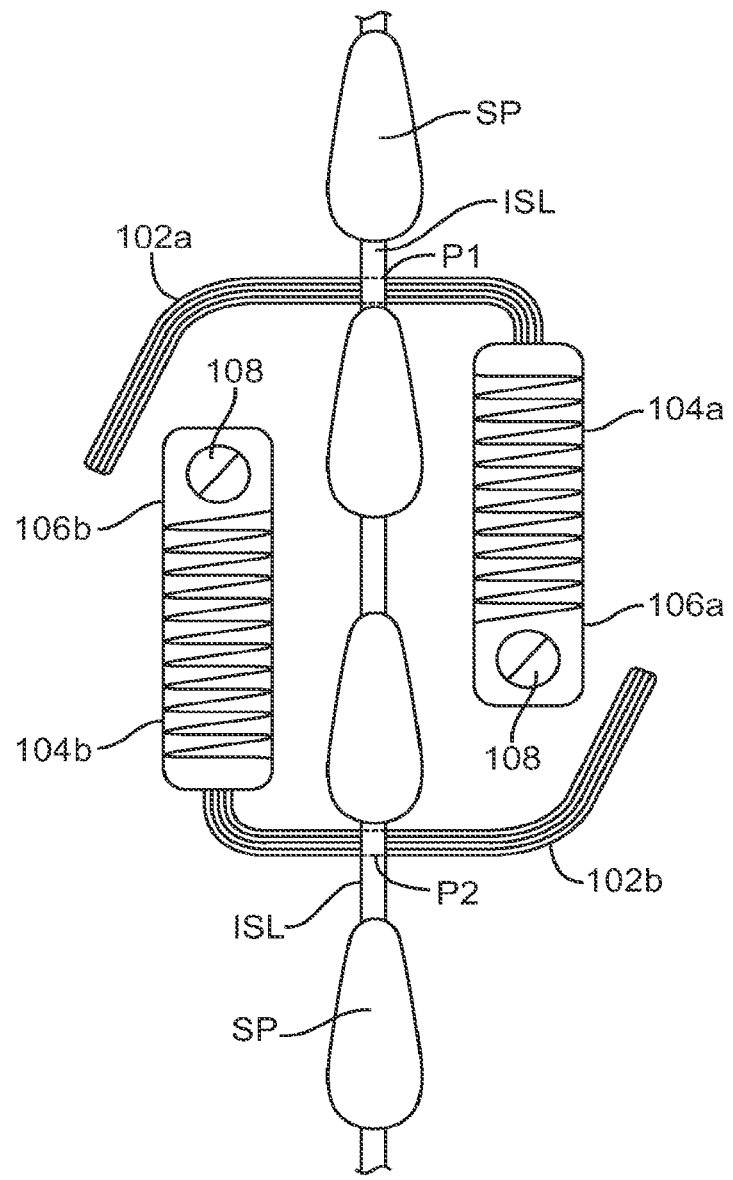
Figure 4K:
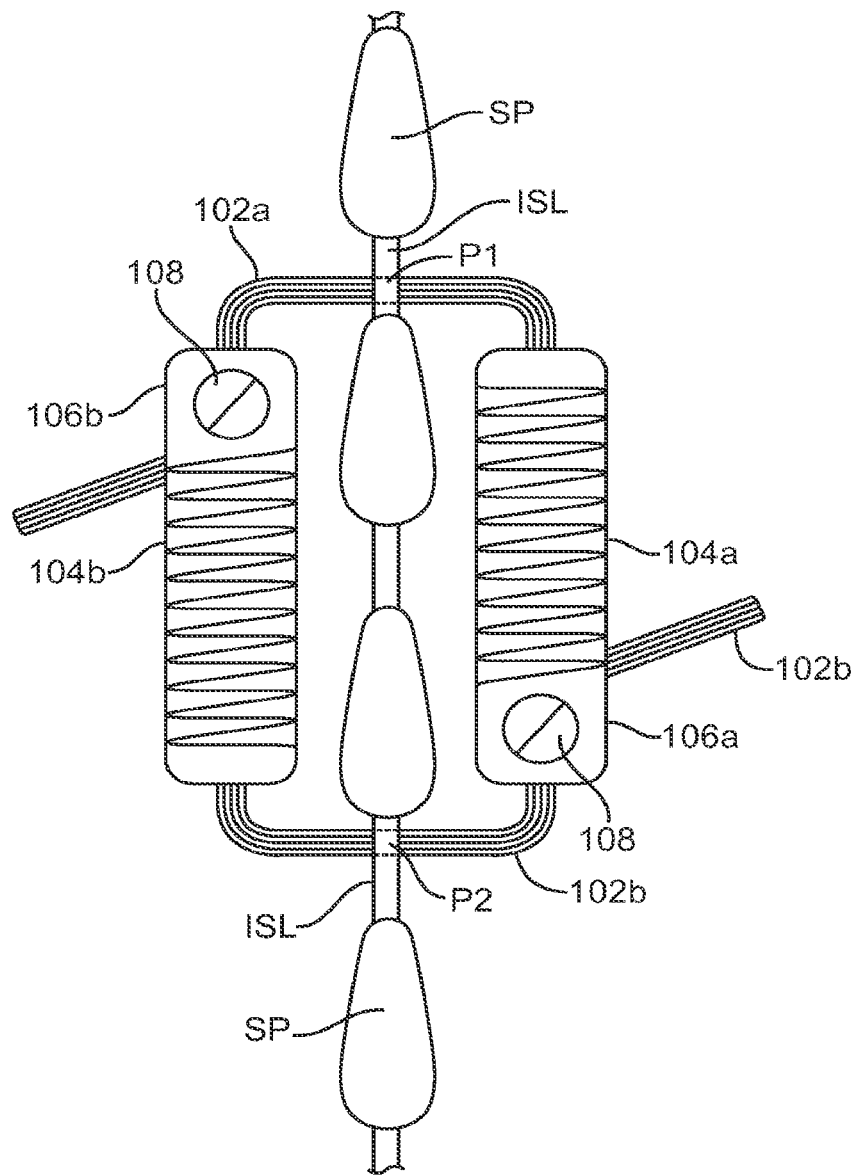

As shown in FIGS. 4H, 4I and 4J, similar to the steps shown in conjunction with the first piercing, tether 102b is pierced through perforation P2 and left in place along with distal tip TI of tool T (best seen in FIG. 4I). Another tool such as a pair of forceps, is then used to grasp distal tip TI to pull tether 102b and compliance element 104b in place relative to the spine, as shown in FIG. 4J. Opposing compliance elements 104a and 104b on opposite sides of spinous processes SP are oriented in opposite directions. Each compliance element 104a, 104b is coupled with their respective tether 102a, 102b and has a respective fastening mechanism or fastening element 106a, 106b. Fastening mechanism 106a, 106b are configured to couple with the tether 102a, 102b of the opposing compliance element 104a, 104b. Further details on exemplary embodiments of fastening mechanisms are disclosed in U.S. patent application Ser. No. 12/479,016 and U.S. Provisional Patent Application No. 61/059,543, the entire contents of which are incorporated herein by reference. For example as shown in FIG. 4K, tether 102a is engaged with compliance element 104b and is then releasably coupled thereto with fastening mechanism 106b. Similarly, tether 102b is also engaged with compliance element 104a and is also releasably coupled thereto with fastening mechanism 106a. Except for their orientation, compliance elements 104a and 104b are identical. One of skill in the art will appreciate that the tether may enter and exit the fastening mechanism in a number of different directions and configurations, and FIG. 4K merely is one exemplary embodiment.

Figure 4L:
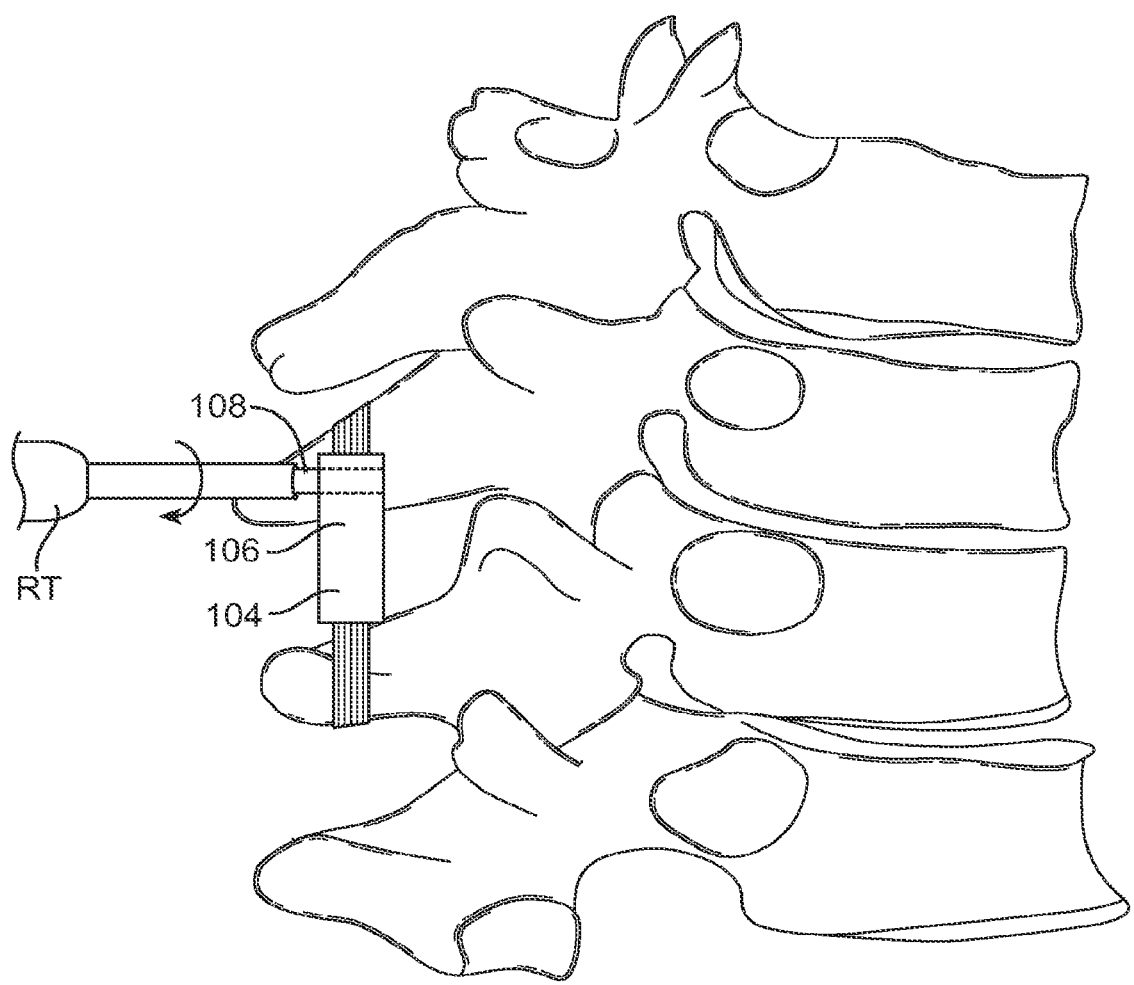
Figure 4M:
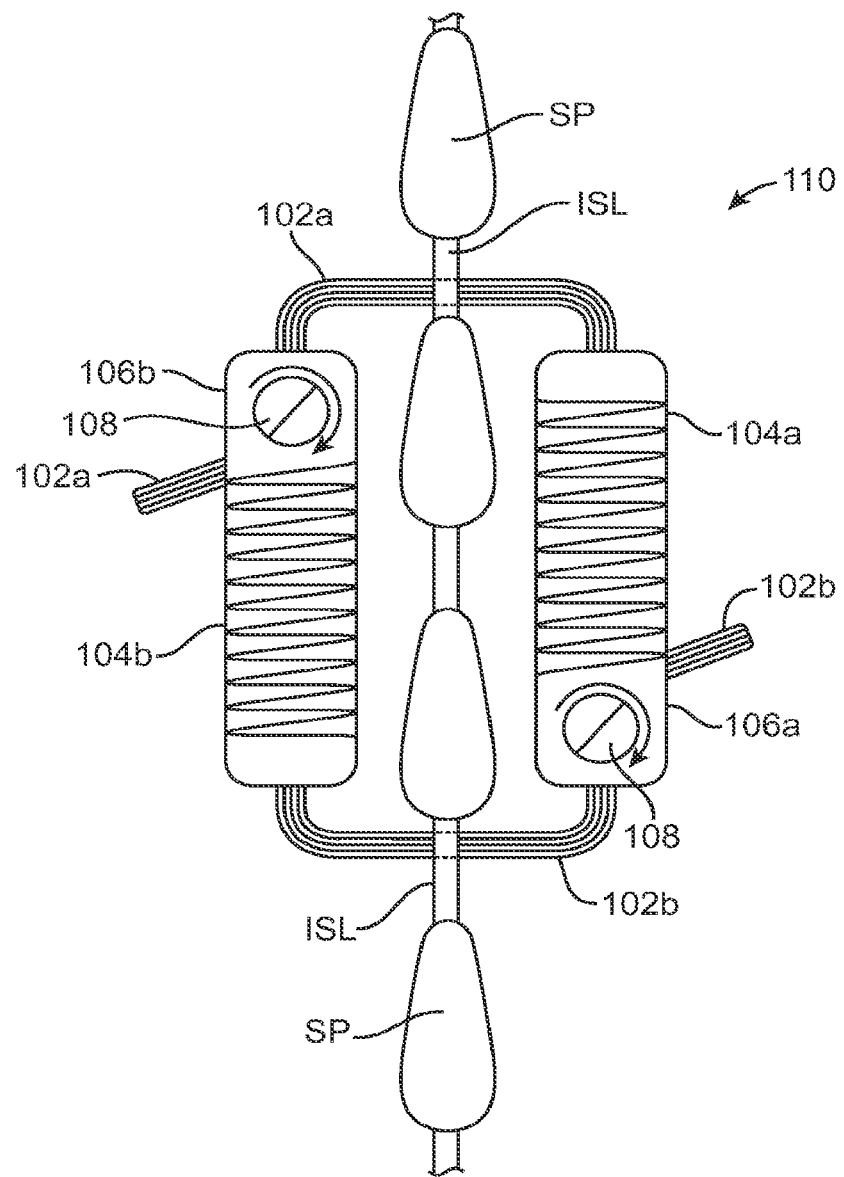

Fastening mechanism 106 may comprise a driver feature 108. As shown in FIG. 4L, the driver feature is adapted to receive a rotating driver tool RT. The driver feature may be a Phillips head, a slotted flat head, a Torx head, a hex head, or the like. Rotation of tool RT, which may be either clockwise or counter-clockwise, changes the configuration of fastening mechanism 106 so as to lock and secure tether 102 in place. This forms a continuous, multi-component tether structure or constraint 110 which couples two spinous processes SP together, as shown in FIG. 4M. Compliance elements 104a, 104b are used to control flexion between spinous processes SP while tethers 102a, 102b and respective fastening mechanisms 106a, 106b contribute to coupling the spinous processes SP together. Depending on the location of the perforations P1 and P2 and the lengths of the compliance elements 104a, 104b, constraint 110 may couple more than two spinous processes SP together. In general, compliance elements 104a, 104b comprise spring-like elements which will elastically elongate as tension is applied through tethers 102a, 102b in an axis generally parallel to the spine. As the spinous processes or spinous process and sacrum move apart during flexion of the constrained spinal segment, the superior tether 102a and inferior tether 102b will also move apart. Compliance elements 104a, 104b each include spring-like elements which will elastically resist the spreading with a force determined by the mechanical properties of the spring-like element. Thus, constraint 110 provides an elastic resistance to flexion of the spinal segment beyond the neutral position. Constraint 110 is often configured to provide a resistance in the range from 7.5 N/mm to 20 N/mm but the resistance may be below 3 N/mm or even below 0.5 N/mm. Constraint 110 may also be adjustable in certain dimensions to allow tightening over the spinous processes or spinous process and sacrum when the spinal segment is in a neutral position. Other, related tether embodiments and joining methods are disclosed in U.S. patent application Ser. No. 12/106,103, U.S. Patent Publication No. 2008/0009866, U.S. Patent Publication No. 2008/0108993, U.S. Provisional Patent Application No. 60/936,897, the entire contents of which are incorporated herein by reference.

In order for the spinous process constraint device of FIGS. 4A-4M to effectively reduce back pain and/or spinal instability, the constraint device should be sized to prevent or limit painful or unstable positions, e.g. the constraint should provide a force resistive to flexion of the spinal segment while still allowing significantly unrestricted extension of the spinal segment. A physician therefore will require methods and apparatus for coupling and adjusting the constraint device to a spinal segment.

Figure 5A:
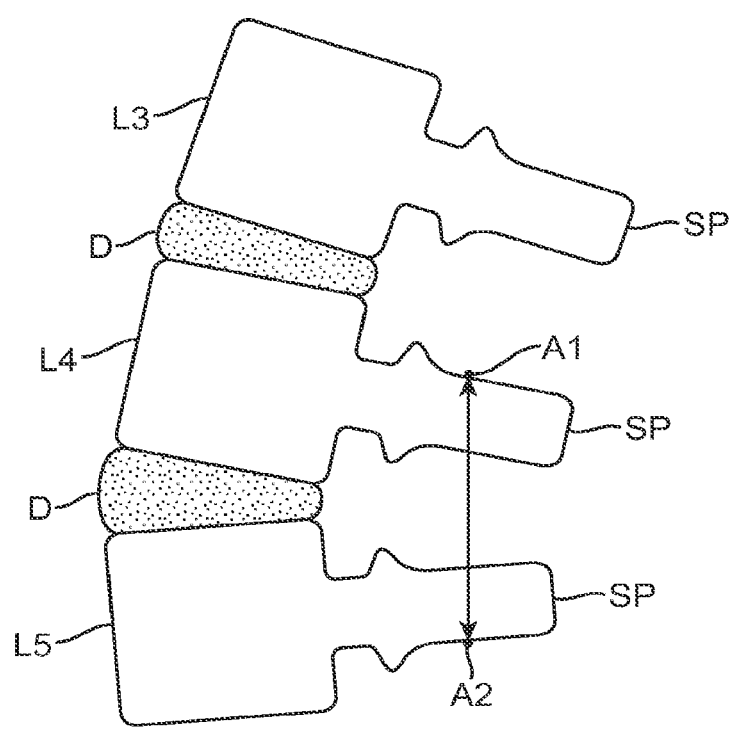
FIGS. 5A-5B show a lateral view of a lumbar region of the spine highlighting different reference points.
Figure 6A:
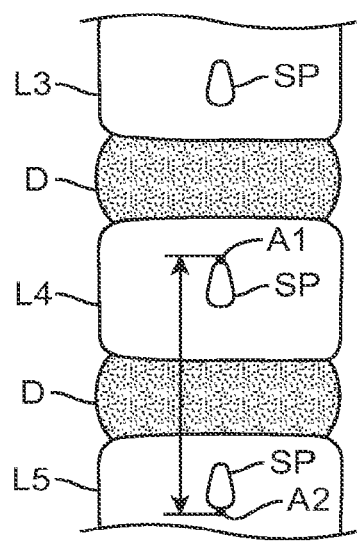
FIGS. 6A-6B illustrate the reference points in FIGS. 5A-5B in a simplified anterior-posterior view of the lumbar region of the spine.

FIG. 5A illustrates a lateral view of a portion of the lumbar region of the spine including lumbar vertebrae L3-L5 having spinous processes SP and discs D disposed between vertebrae. One exemplary method of determining the appropriate size of the constraint device involves obtaining a pre-operative image, such as a radiograph, of the affected spinal segment. The radiograph is taken while the patient is in a desired, preferably pain-free posture so that the spinal segment is in the final desired neutral position for the device. From the radiograph, two reference points are selected and these reference points are used to estimate the size to which the constraint device should be adjusted. Additionally, radiopaque gauges may be used to help determine magnification and distortion effects in the radiograph. A scale may be used in the radiograph for measuring the distance between reference points and the physician may compensate for magnification and/or image distortion. In a preferred embodiment, a first reference point A1 is selected on a superior surface of a first spinous process SP coupled to a first vertebra and the second reference point A2 is selected on an inferior surface of a second spinous process coupled to a second vertebra. The second vertebra is below the first vertebra when the patient is in the standing position. The length between points A1 and A2 define a target distance as indicated by the arrow in FIG. 5A. Thus, once the constraint device is applied to the spinal segment, it may be adjusted intra-operatively until the distance between reference points A1 and A2 is returned to the pre-operative target distance. This helps to ensure that the constraint device is in a neutral position when the patient is standing but will provide a force resistive to flexion of the spinal segment while still allowing significantly unrestricted extension of the spinal segment. The target distance may be measured with calipers, rulers, digital radiographic measurements or other suitable gauges. After the distance between reference points A1 and A2 have been measured and adjusted, a verification step may be performed in order to ensure that the proper distance is maintained prior to completing the surgical procedure. If the distance has changed from the target value, the surgeon may re-adjust the constraint device in order to reposition the spinous processes so that the distance between the two reference points A1, A2 is brought closer to the target distance. This fine tuning and re-adjustment may be repeated as required. FIG. 6A illustrates a simplified anterior-posterior view of the spinal segment seen in FIG. 5A. The target distance may also be estimated using an anterior-posterior radiograph instead of, or in conjunction with the lateral radiograph.

Figure 5B:
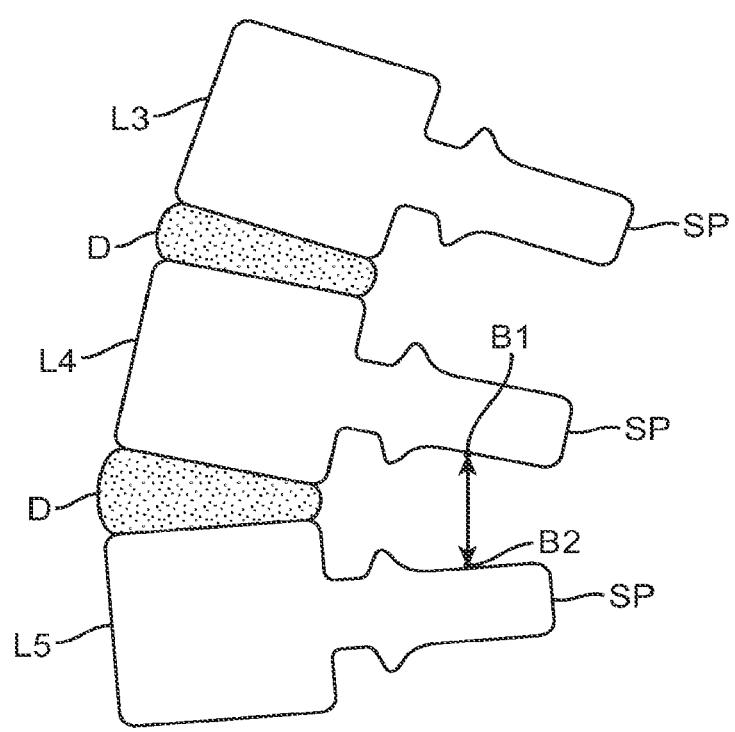
Figure 6B:
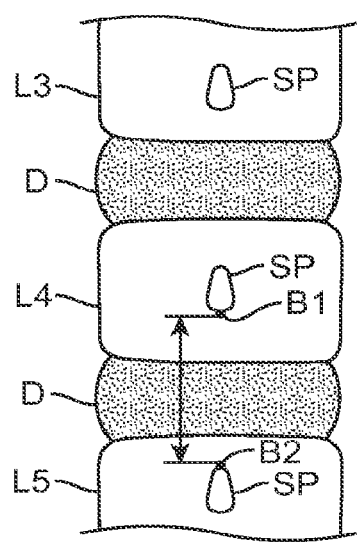

In another preferred embodiment, the two reference points may be located along different regions of the spinous processes. For example, FIG. 5B illustrates the same view of the spinal segment as in FIG. 5A, yet here, the first reference point B1 is located along an inferior surface of a first spinous process coupled to a first vertebra and the second reference point B2 is on a superior surface of spinous process coupled to a second vertebra. The second vertebra is below the first vertebra when the patient is in a standing position. A radiograph or other image of the spinal segment while the patient is in a preferred posture such as standing, may be used to obtain the pre-operative length between points B1 and B2 and this is used to define the target distance as indicated by the arrow in FIG. 5B. This length may be used to control adjustment of the constraint device in a manner similar to that previously described with reference to FIG. 5A. One advantage of using the reference points illustrated in FIG. 5B is that it may be easier to measure this distance intra-operatively using calipers, rulers, gauge pins or sizing blocks than measuring the distance between reference points in FIG. 5A. In FIG. 5B, the distance is an "inside" dimension as opposed to the "outside" dimension in FIG. 5B and thus may be easier to measure at a consistent location. Adjustment, verification and re-adjustment may also be performed as previously disclosed above. FIG. 6B illustrates a simplified anterior-posterior view of the spinal segment illustrated in FIG. 5B. The target distance may also be estimated using an anterior-posterior radiograph instead of, or in conjunction with the lateral radiograph. Once the constraint device size has been set to the target value, optional further adjustment of the device allows a physician to set a desired pre-tension value. In still other embodiments, the measured distance may be the distance between superior surfaces of both spinous processes.

Figure 7A:
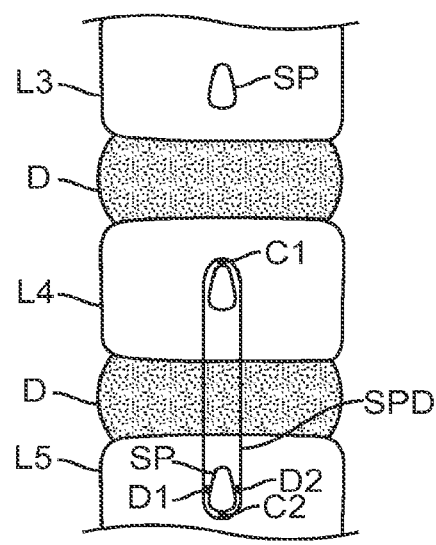
FIGS. 7A-7B illustrate a simplified anterior-posterior view of a lumbar region of the spine highlighting a plurality of reference points that may be used to estimate prosthesis circumference.
Figure 7B:
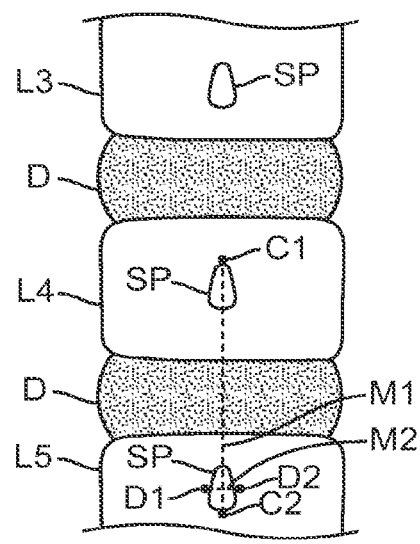

Another embodiment of a sizing algorithm estimates the circumference of the spinous process constraint device from the pre-operative radiograph of the affected spinal segment. FIG. 7A illustrates an anterior-posterior view of a portion of the lumbar region of the spine. This includes lumbar vertebrae L3-L5 having spinous processes SP and discs D disposed between vertebrae. A spinous process constraint device SPD encircles two spinous processes SP. In this example, the two spinous processes are adjacent one another, however in other embodiments, one or more spinous processes may be disposed in between the two spinous processes to which the spinous process constraint device is coupled. A first pair of reference points may be selected on the pre-operative radiograph to help estimate the circumference to which the spinous process constraint device should be adjusted. In FIG. 7A, a first reference point C1 is disposed on a superior surface or slightly thereabove of a first spinous process coupled with a first vertebra and a second reference point C2 is disposed on an inferior surface or slightly therebelow of a second spinous process coupled with a second vertebra. The first vertebra is cranial, or above the second vertebra when the patient is in a standing position. The reference points C1 and C2 define a major axis and have a major axis length. The major axis length may be measured from the radiograph using calipers, a ruler or other measuring techniques including those previously discussed above. Additionally, the physician may adjust measurements to account for distortion or magnification in the radiograph. The major axis is shown by the vertical dotted line extending through C1 and C2 in FIG. 7B. The major axis length may also be estimated from a lateral view of the affected spinal segment. The circumference of the spinous process constraint device SPD may be estimated as twice the major axis length plus a constant which accommodates for the constraint device wrapping around the apex of the upper and lower spinous processes. The constant may be measured from the radiograph or obtained from a lookup table based on other characteristics of the patient's body (e.g. height, body type, etc.).

A second pair of reference points optionally may also be selected on the pre-operative radiograph to further help estimate the adjusted size of the spinous process constraint device SPD. In FIG. 7A, reference points D1 and D2 are taken on either side of one of the spinous processes SP around which the constraint device SPD is encircled. FIG. 7A shows D1 and D2 on either side of the inferior spinous process, but they may also be located on either side of the superior spinous process. Reference points D1 and D2 define a minor axis transverse to the major axis and having a minor axis length. The minor axis is illustrated by the dotted line extending through points D1 and D2 in FIG. 7B. Minor axis length may be similarly measured as the major axis length.

Once major axis length and optional minor axis length have been measured from the pre-operative radiograph or other pre-operative image, the circumference of the spinous process constraint device may be estimated. The spinous process constraint device circumference may be estimated as a rectangle and thus is calculated as twice the major axis length plus twice the minor axis length. The constraint device circumference may also be estimated using other models such as by calculating the circumference of an oval or ellipse. Furthermore, the major axis length and minor axis length may be correlated to constraint device circumference and a lookup table may provide the corresponding adjustment size to use. Once the constraint device is implanted around the spinous processes, its size is adjusted until its circumference matches the calculated value or the value provided by the lookup table. The circumference of the constraint device may be measured directly or calibration markings on the constraint device may be used to indicate constraint device size. Once the constraint device size has been set to the target value, optional further adjustment of the device allows a physician to set a desired pre-tension value.

Figure 8A:
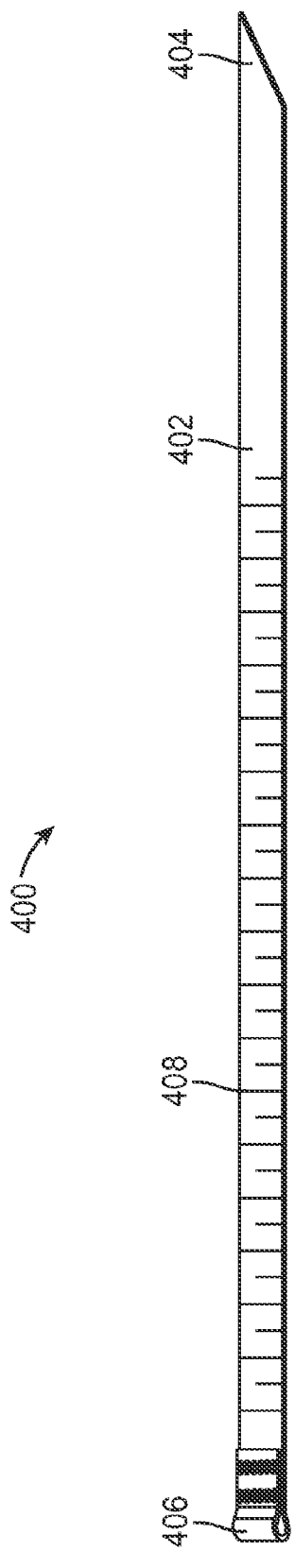
FIGS. 8A-8B illustrate an exemplary embodiment of calibration markings on a spinous process constraint device.
Figure 8B:
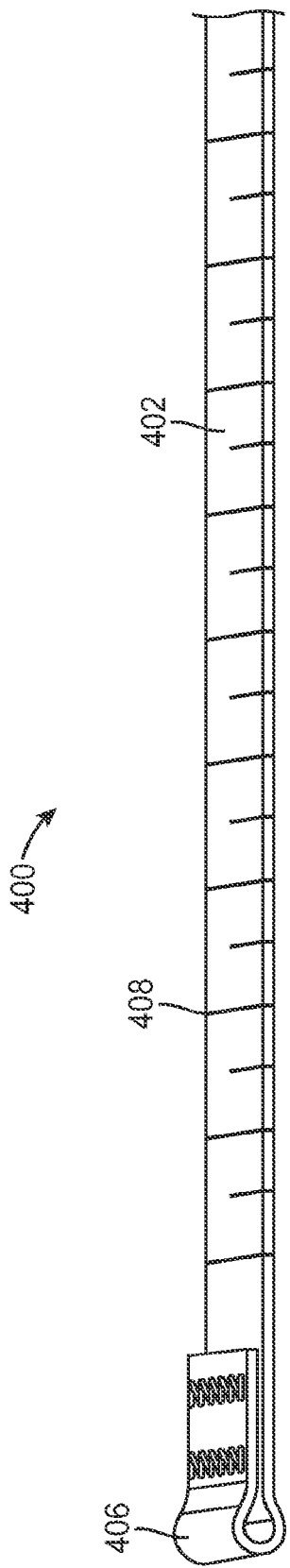

FIGS. 8A-8B illustrate an exemplary embodiment of calibration markings that may be included on the spinous process constraint device to help estimate device length or circumference. In FIG. 8A, the tether portion 402 of a spinous process constraint device 400 is illustrated. The tip 404 of the tether is cut at an angle and opposite end 406 is folded against itself and secured to form an aperture that may be coupled with a compliance element having a locking mechanism (not illustrated). The angle on the tip allows that end to easily be inserted into a locking mechanism of this or another spinous process constraint device when two or more devices are coupled together. Calibration markings 408 may be printed, etched or otherwise affixed to the tether portion 402 of the device. Calibration markings 408 may be spaced apart at a known distance from one another or numbers may also be included with the markings to facilitate reading. The calibration marking may indicate tether length or circumference or another parameter that allows the physician to adjust the tether to the target value estimated from the pre-operative standing radiograph. FIG. 8B is an enlarged view of FIG. 8A.

In addition to estimating device length or circumference, it may also be desirable to characterize the patient's lower lumbar spine in various positions to establish a threshold position where pain is experienced. Once this threshold position is determined, the constraint device may be applied to the patient's spine and adjusted to help ensure that the patient's back remains at or below the threshold position. Thus clinical evaluation of flexion exacerbated pain may be linked with imaging based diagnostic techniques and various factors may be quantified in the characterization of lower back pain. For example, the amount of flexion that causes or exacerbates pain or subluxation of facet joints may be measured and the ability of the native tissue structures to resist flexion or translation may be determined. The nature and degree of any instability may also be evaluated. The presence and shape of spinous processes on the sacrum may also be evaluated for coupling with a constraint device. The shape of spinous processes may also be evaluated along with a determination of whether modification of the spinous processes is required for receiving the constraint device. Also, the stiffness, size and/or tension of the constraint device used to limit flexion may be estimated in order to best treat a specific patient.

Figure 11A:
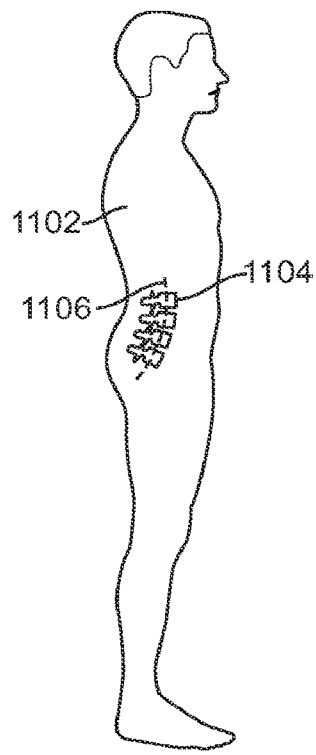
FIGS. 11A-11C illustrate curvature of a patient's spine in different postures.
Figure 11B:
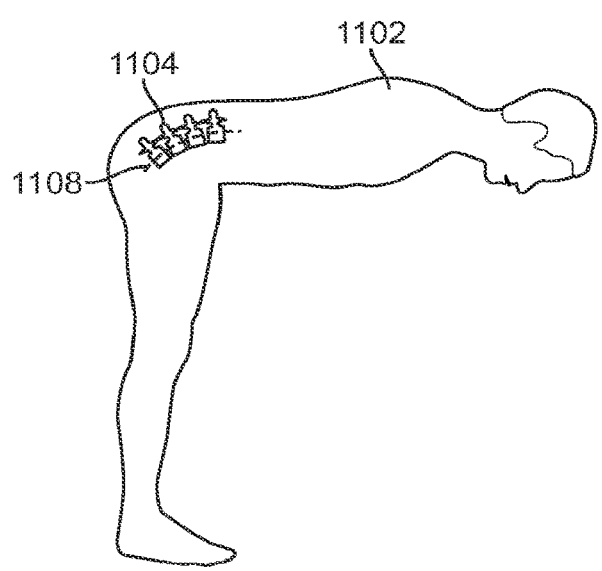
Figure 11C:
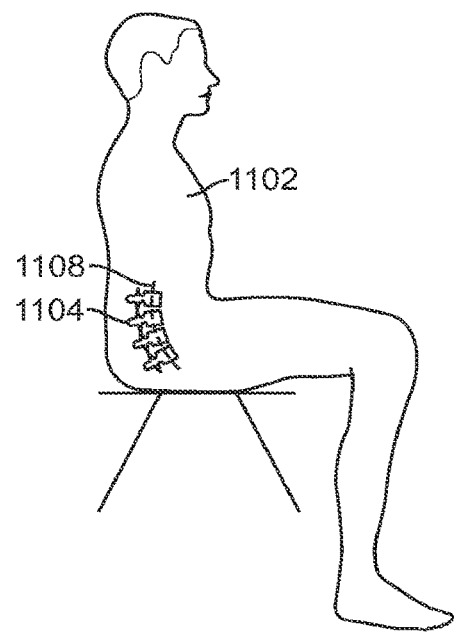

FIGS. 11A-11C illustrate the curvature of a patient's lower lumbar spine when the patient is in different postures. In FIG. 11A, the patient 1102 is in a neutral, standing position and the lower lumbar spine 1104 has a dorsally-concave curvature indicated by dotted line 1106 that is referred to as lordosis. When the spine flexes, as in a forward bending (FIG. 11B) or a seated posture (FIG. 11C), the lordotic curvature of the lumbar spine flattens out. As the spine continues to flex the curvature may shift to anterior concavity, as illustrated by dotted line 1108. This is referred to as kyphosis.

Flexion exacerbated pain is often referred to as mechanical low back pain and involves pain when the spine is in a flexed posture. Flexion exacerbated pain may be associate with degeneration of the intervertebral disc (the degenerative cascade is described in greater detail by Kirkaldy-Willis). Prior diagnostic techniques often focused more on degenerative disc disease as the basis of the clinical evaluation, including plain film x-ray analysis of disc height, range of motion (ROM) and MRI based (magnetic resonance imaging) grading of disc degeneration (e.g. the Pfirrmann MRI classification system).

Figure 12A:
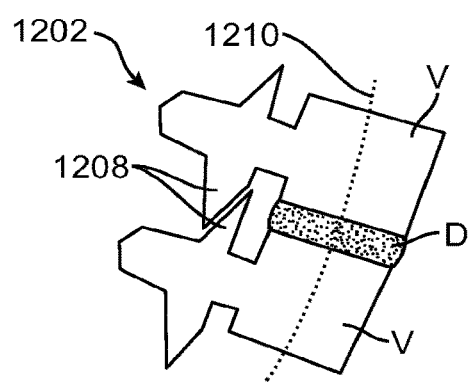
FIGS. 12A-12B illustrate a spinal motion segment in kyphosis and lordosis.
Figure 12B:
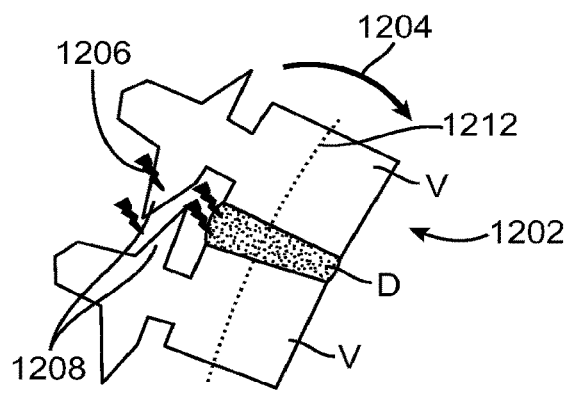

FIG. 12A illustrates a spinal segment 1202 having two vertebrae V and a disc D with overlapping facet joints 1208. The spinal segment is often pain free in a neutral (lordotic) posture as indicated by dotted line 1210. However, the segment may become more painful as the segment flexes, as illustrated in FIG. 12B. The flexion 1204 changes the curvature of the spinal segment from lordosis to kyphosis as indicated by dotted line 1212 resulting in pain 1206. The amount of flexion that causes pain may vary from patient to patient.

Figure 13A:
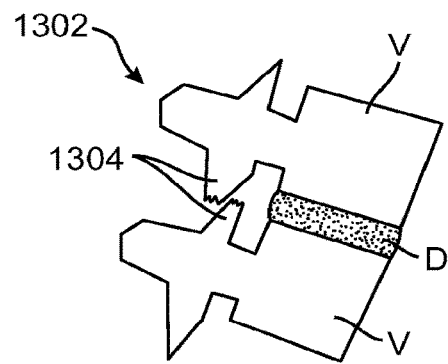
FIGS. 13A-13B illustrate a spinal motion segment with degenerative spondylolisthesis.
Figure 13B:
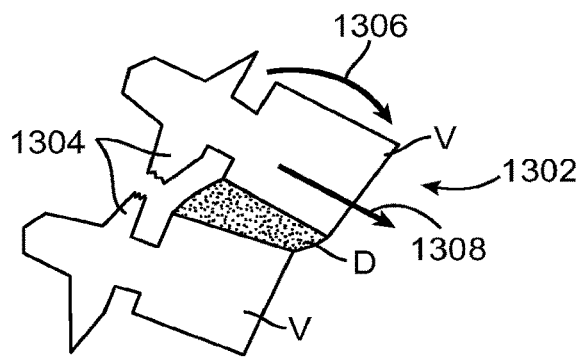

Other pathologies such as degenerative spondylolisthesis (DS) may be exacerbated by flexion as well. In DS, degeneration of the facet joints reduces the motion segment's inherent ability to resist shear translation. This is exacerbated in flexion as facet joint engagement decreases. FIG. 13A illustrates a spinal motion segment 1302 having two vertebrae an a disc D. The facet joints 1304 have degenerated and thus do not overlap as much as healthy facet joints (e.g. as illustrated in FIG. 12A). As the spinal segment 1302 is moved into flexion 1306, the facet joints 1304 separate from one another and thus are less able to resist shear movement 1308 of one vertebra V relative to the other vertebra V and thus they move, distorting the disc D and causing pain as illustrated in FIG. 13B. Typical diagnostic techniques for degenerative spondylolisthesis focus on neurological symptoms and assessment of gross mechanical instability (e.g. range of motion and intervertebral translation).

Plain-film radiographs (x-rays) may be taken with the patient in various postures, to determine what posture causes pain or instability. X-rays may be used to measure intervertebral disc angle, inter-spinous process or pedicular distance for preoperative planning and sizing of any implant. For example, a patient may be told to bend forward until pain is felt. An X-ray taken in this posture will indicate to the clinician the segmental posture that elicits pain. This posture represents a threshold position above which the patient experience pain and below which pain is either reduced or eliminated. FIG. 14A illustrates a patient 1402 bending forward so that the lumbar spinal segment 1404 is in flexion 1406 and FIG. 14B illustrates the patient 1402 standing up so that the spinal segment 1404 is in the neutral position. The patient may actuate a button or switch to indicate that the pain has started or stopped. The switch may be integrated with the radiography equipment so that the image is captured at the pain threshold and other postures.

Because radiographic images of spinous processes can be variable (particularly when cartilaginous tissue is present), radiopaque markers may be used to provide consistent landmarks/fiducials to measure anatomic parameters. For example, tantalum beads may be implanted into the spinous processes to enable consistent measurement of the separation of the spinous processes. With the beads providing a consistent reference for measurement, the desired (likely pain-free) posture may be more reliably reproduced in the operative setting.

In addition to evaluating pain vs. posture, this technique may evaluate other posturally-dependent attributes such as facet-engagement. Engagement of the facet joints decreases with segmental flexion, which may exacerbate conditions such as degenerative spondylolisthesis. Radiographs may be used to determine the posture at which the facet joints begin to sublux and resistance to shear load and translational motion is reduced. Then, the techniques described above may be used to apply and adjust the flexion constraint in order to prevent these postures. FIG. 15A illustrates a lumbar spinal motion segment 1502 having two vertebrae V, a disc D, and facet joints 1504. The spinal segment 1502 is in flexion 1506 while the spinal segment in FIG. 15B is in the neutral position where the spinal segment has a lordotic curve 1508. The distance between spinous processes SPD may be measured along with the intervertebral disc angle IVDA from the radiographic images, and these parameters may be used to characterize the threshold position. Anatomical measurements from radiographs in painful (FIG. 15A) and pain-free or reduced pain (FIG. 15B) postures may assist a surgeon in correctly positioning the patient on the operating table, and applying the correct size or tension to a flexion-constraining implant. The objective being to implant the constraint such that pain-free motion is permitted, while the painful or unstable motions are restricted. Measurements of interest may include the distance between spinous processes (SPD) and intervertebral disc angle (IVDA).

Plain-film radiographs and resulting measurements may also be correlated to postural measurements of flexion during a patient's normal activities of daily living to determine modes and frequency of motions that cause pain. For example, a patient may be fitted with a goniometer that measures spinal flexion, or strain gauges on the skin of the lower back. Measurements from the goniometer or strain gauges can be correlated to radiographic measurements described above to estimate lumbar flexion. The patient wears the device during their normal routines, possibly for a day or a week. The device records lumbar flexion, as well as inputs by the patient to indicate pain. Data recorded by the device can inform the physician regarding the mode, frequency and postural dependency of the patient's pain.

The patient's spine may be manually manipulated by the physician, to effect a pain-free posture, evaluate segmental instability, or post-operative effectiveness of treatment. In a clinical, diagnostic setting, this will typically be done by pushing against the lower lumbar spine to create a lordotic curve (much as a back brace in a car seat works to support the curvature of the spine). A frame or chair with an adjustable lumbar bolster (such as a plunger) may be used to apply a repeatable manipulation to the spine. Alternatively, hip flexion (via the seat angle) may be used to manipulate the spinal posture. These techniques may also use a proximally-directed force through the femoral head and hip to antevert the pelvis (rotate forward), and thus induce the lordotic curvature. The proximally-directed force through the femoral head will typically be accomplished by applying a force or restraint to the knee.

These methods and systems may be used by the physician to assess lumbar postures which are painful vs. pain-free. As described above, the patient may actuate a switch to indicate the pain threshold. The switch could provide a time-stamp for dynamic radiography, or trigger an x-ray machine to capture an image. If the frame or chair is radiolucent, then radiographic images may further enable the physician to reproduce the pain-free posture intra-operatively and apply the constraint structure so that it will prevent motion into the painful posture. Also as described above, implanted radiopaque markers such as tantalum beads may provide consistent reference points for radiographic measurements.

Figure 16A:
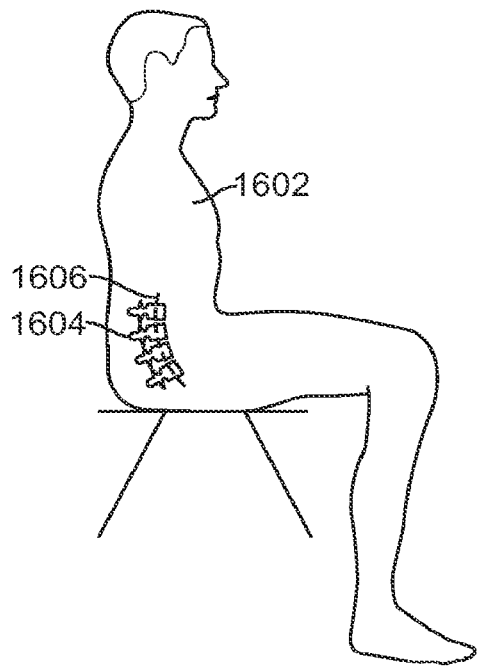
FIGS. 16A-16C illustrate application of a lumbar force to a patient's lower back.
Figure 16B:
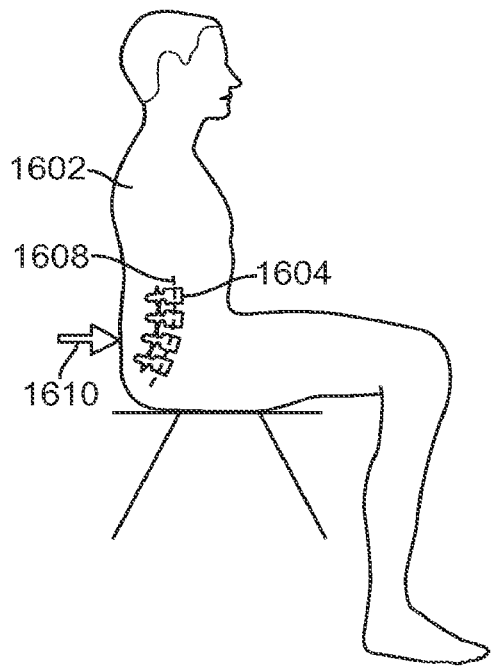

FIG. 16A illustrates a normally painful posture where a patient's 1602 spine 1604 is flexed 1606. The patient may be sitting or the patient may be in any other position where the spine is in flexion. FIG. 16B shows how pain is relieved with application of a force 1610 or support that restores lordosis 1608 in the lumbar spine 1604 (similar to the lumbar support in car seats). Radiographic images in the manipulated, pain-free posture may be used as described above to implant a flexion constraint device such that a spinal alignment is altered to relieve pain, in a previously-painful posture.

Figure 16C:
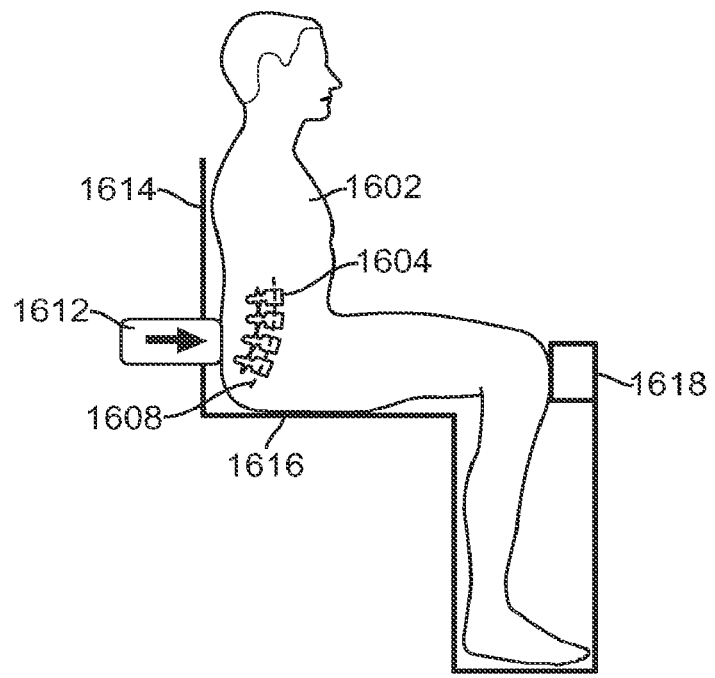

Diagnostic spinal manipulation, as described above, may be performed more repeatably with a system to apply consistent postural manipulation. One example is a chair as seen in FIG. 16C. The patient 1602 is sitting in the chair having a seat 1616, a back 1614, and a knee brace 1618. A plunger 1612 can apply manipulative pressure to the lumbar spine 1604, and the knee brace 1618 helps maintain the patient in a desired position. The chair preferably is radiolucent so that radiographs may be obtained and used to implant a flexion constraint as described previously.

An apparatus which may be used for this purpose and operates on principles similar to the system illustrated above, is the commercially available "Nada Chair" (http://www.nadachair.com/). A strap looped around the lumbar spine provides lordosis-restoring lumbar support. The opposite end of the strap is looped around the knees so that it can be tensioned and apply forces to both the lumbar spine and femoral head (via the knee). Such an apparatus may be used to apply mechanical manipulation to the lumbar spine and determine the postural effect on pain. Other braces or orthoses may similarly be used to diagnose flexion-exacerbated, postural pain.

Manual or mechanical manipulation may also be used intraoperatively to assess segmental biomechanics and instability. The surgeon may use an adjustable table (such as the Jackson Axis table), or instruments such as laminar spreaders or the Mekanika Spinal Stiffness Gauge device to measure ranges of motion or segmental stability to determine the amount and type of restabilization needed from the flexion constraint. This may be particularly useful for potentially-destabilizing procedures, such as a decompression, where segmental stability may be assessed before and after the decompression procedure to understand how the segmental biomechanics were affected by the procedure. For example, a surgical instrument may measure applied load and displacement of vertebral structures (typically the spinous processes or laminae) to assess a linear stiffness of the spinal structure (usually in N/mm). With the linear stiffness and a measurement or estimate of the distance from the surgical instrument to the segmental center of rotation (COR), the segmental bending stiffness can be estimated, usually in Newton-meters per degree. This may be calculated as:

$$K = 0.001 \frac{P}{\Delta L} R^2 \frac{\pi}{180°},$$

where
K is segmental bending stiffness (usually in N-m/deg);
P is the load applied by the surgical instrument (usually in N);
$\Delta L$ is the distraction or compression applied by the instrument (usually in mm);
R is the moment-arm, or distance from the instrument to the segmental center of rotation (usually in mm); and
The factor 0.001 is used to accommodate the variable L and R being in millimeters, while the variable K is in Newton-meters/degree.

Figure 17:
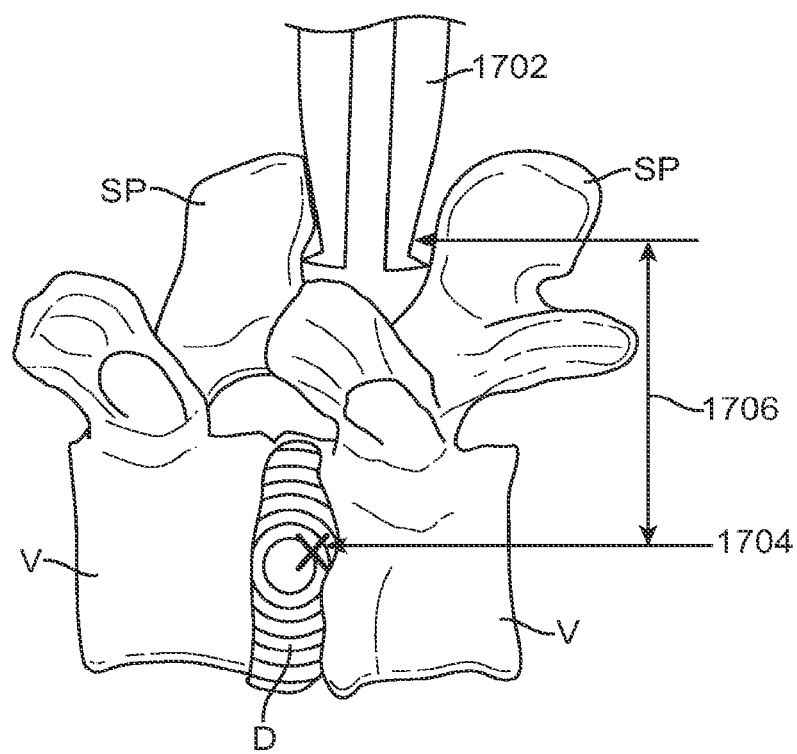
FIG. 17 illustrates measurement of various features a spinal segment.

FIG. 17 shows a spinal motion segment having two vertebrae V separated by a disc D and schematically illustrates these measurements. A surgical instrument 1702 is inserted between the spinous processes SP of adjacent vertebrae V and measures the distraction or compression, and the load applied to the vertebral structures. The moment arm 1706 is distance from the center of rotation 1704 of the motion segment to the surgical instrument 1702. With an assessment of segmental bending stiffness, the surgeon can make decisions about appropriate instrumentation for stabilization (e.g. spinal rods), as well as stiffness and tightness of the instrumentation. A template, look-up table, software program or other algorithm may be provided with an implant system to make such decisions with these measurements. In one exemplary embodiment, a system for providing an elastic resistance to flexion may come in multiple stiffnesses. A table provided for use with the implant systems may recommend which stiffness is appropriate for a particular patient based on intraoperatively-measured parameters.

Dynamic radiography, such as obtained from video fluoroscopy or several frames of x-ray imaging, may also be used to assess instabilities with more specificity and resolution. In degenerative spondylolisthesis, dynamic radiography may help to identify the intervertebral angle at which the facets become unstable. Quantitative motion analysis of the vertebrae may further identify the nature of flexion instability of a specific motion segment. For example, as the entire spine moves into flexion, a greater portion of the motion may occur at a single motion segment, indicating flexion instability in that segment. Furthermore, the instability may present predominantly within a specific portion of the total range of motion. Use of these diagnostic, dynamic radiographic techniques may enable the physician to apply a constraint to flexion which allows as much natural motion as possible, while preventing pathologically unstable or painful flexion motions. Similar dynamic radiographic measurements may be used to assess the biomechanical efficacy of any treatment.

As described above, the patient may use a switch to indicate the pain threshold, possibly as a timestamp on the dynamic radiograph. The dynamic radiographs may also be used to determine facet joint engagement or subluxation, or intervertebral translation, across the range of motion. Implantable, radiopaque markers may provide consistent measurement references that enable the surgeon to reproduce a desired posture intraoperatively. These techniques may then be used to apply the flexion constraint such that undesired postures are restricted.

Figure 18:
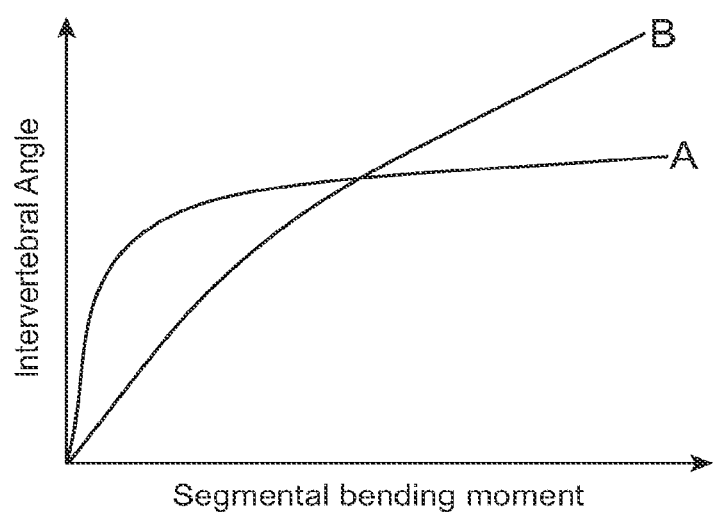
FIG. 18 illustrates the relationship between intervertebral angle and segmental bending moment under various conditions.

FIG. 18 graphically illustrates the relationship between intervertebral angle and segmental bending moment in two different situations. Dynamic radiography may help to identify the nature of an instability, such as instability around the neutral zone (curve A), vs. hypermobility or excessive total ROM (curve B). The nature of the instability may affect the application of the constraint device. For example curve A may require the constraint to be implanted more tightly; while curve B may require a stiffer constraint.

Figure 19A:
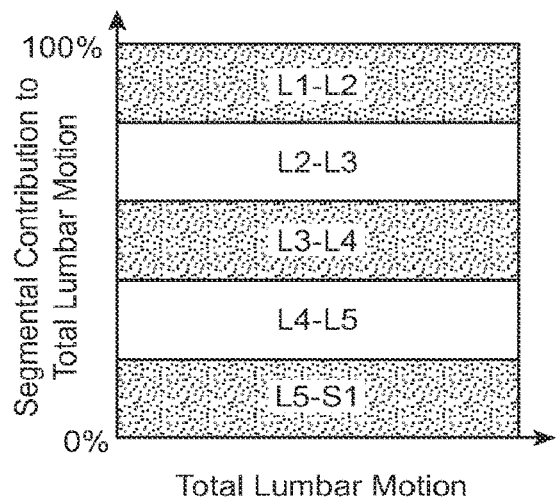
FIGS. 19A-19B illustrate the segmental contribution to total lumbar motion versus total lumbar motion under various conditions.
Figure 19B:
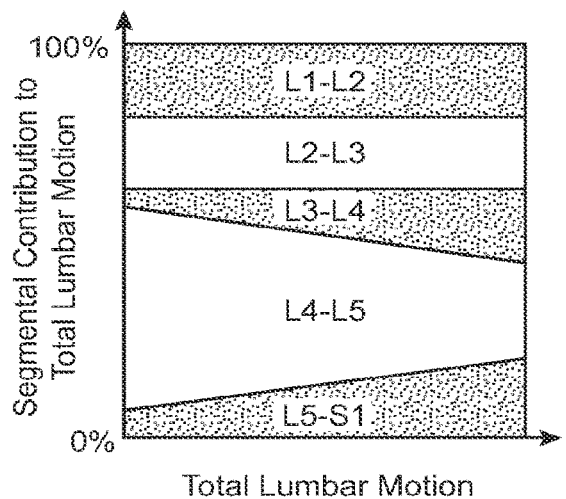

FIGS. 19A-19B graphically illustrate the relationship between segmental contribution to total lumbar motion and total lumbar motion in two different situations. Dynamic radiographs can show the relationship between different motion segments through the total range of motion. FIG. 19A illustrates five motion segments flexing equally throughout the total range of lumbar motion. FIG. 19B illustrates five motion segments, where the L4-L5 segment accounts for the largest share of motion as the spine begins to flex. However, the total range of motion for the five segments is the same. Dynamic radiography may detect the early-phase instability of L4-L5, whereas conventional x-rays may show simply that all segments have the same total range of motion. Understanding the nature of the segmental instability allows the physician to appropriately apply the flexion constraining implant.

Figure 20:
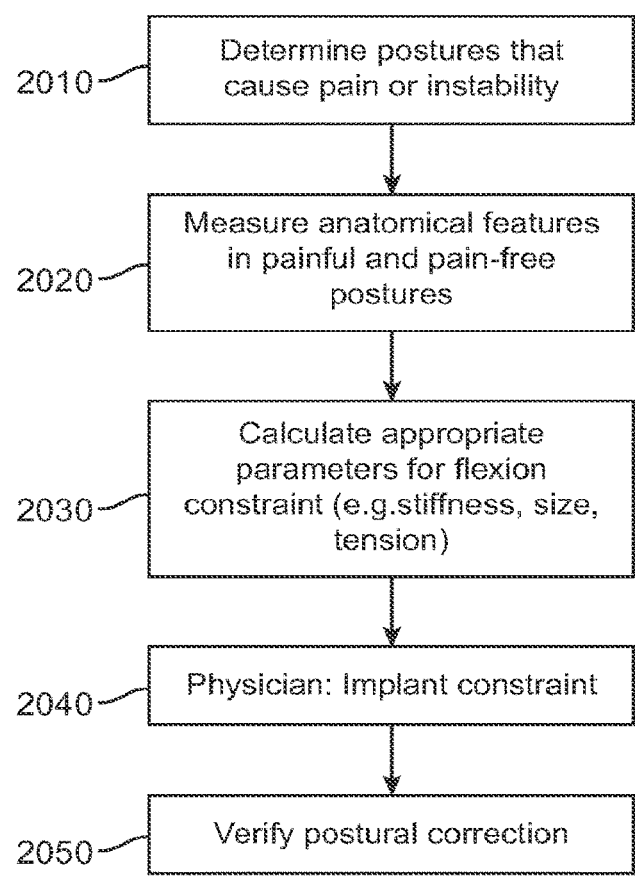
FIG. 20 illustrates an exemplary algorithm for diagnosing and treating lower back pain.

Any of the diagnostic and treatment techniques described above may utilize software as part of the process. Software may facilitate measurement of the anatomical properties, such as intervertebral disc angle, tissue stiffness, strain, or dynamic motion properties. The software package may use these measurements to calculate the appropriate parameters of the flexion constraint implant, such as the appropriate size, stiffness or tension. The software may intra- or post-operatively verify that the constraint is implanted such that it has the intended biomechanical effect. An exemplary method is illustrated in FIG. 20 where the posture that causes pain or instability is first determined 2010 and then anatomical features are measured in the painful and pain-free or reduced pain postures 2020. Appropriate parameters for a flexion constraint are calculated (e.g. stiffness, size, tension, etc.) 2030 and the surgeon then implants the constraint 2040. The postural correction may then be verified 2050.

As previously described above with respect to FIGS. 4A-4M, the spinous process constraint device often includes one or more compliance elements positioned on opposite sides of a spinous process, across the spinal segment midline. The compliance elements act like springs to help provide the force resistant to flexion of the spinal segment as the spinous processes move away from one another. Because of the compliance element, adjusting the device to position the spinous processes at a target distance from one another or to provide a target prosthesis size such as circumference may be difficult. As the device is tensioned, the compliance element will elongate and prevent the determination of the reference distance. It would therefore be advantageous to provide a constraining tool that can prevent elongation of the compliance element during adjustment of the constraint device. The constraining tool may be used during the deployment and implantation procedure previously described. The constraining tool is applied to the compliance element to temporarily restrict its elongation or limit extension to a desired value, during adjustment of the device length or circumference. Once the compliance element is adjusted, the constraining tool may be removed. A physician may then continue to adjust the constraint device in order to establish a desired pre-tension therein.

Figure 9A:
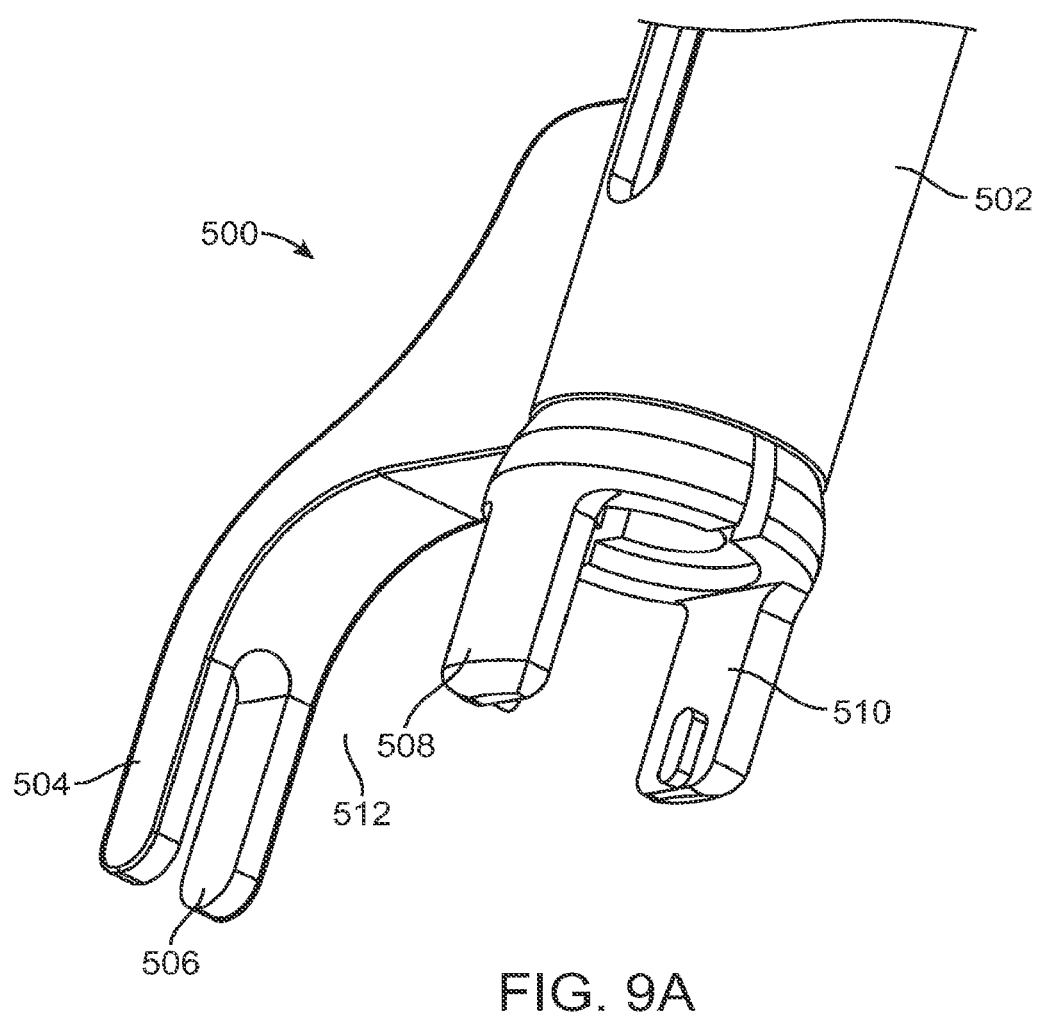
FIGS. 9A-9C illustrate an exemplary embodiment of a constraining tool.
Figure 9B:
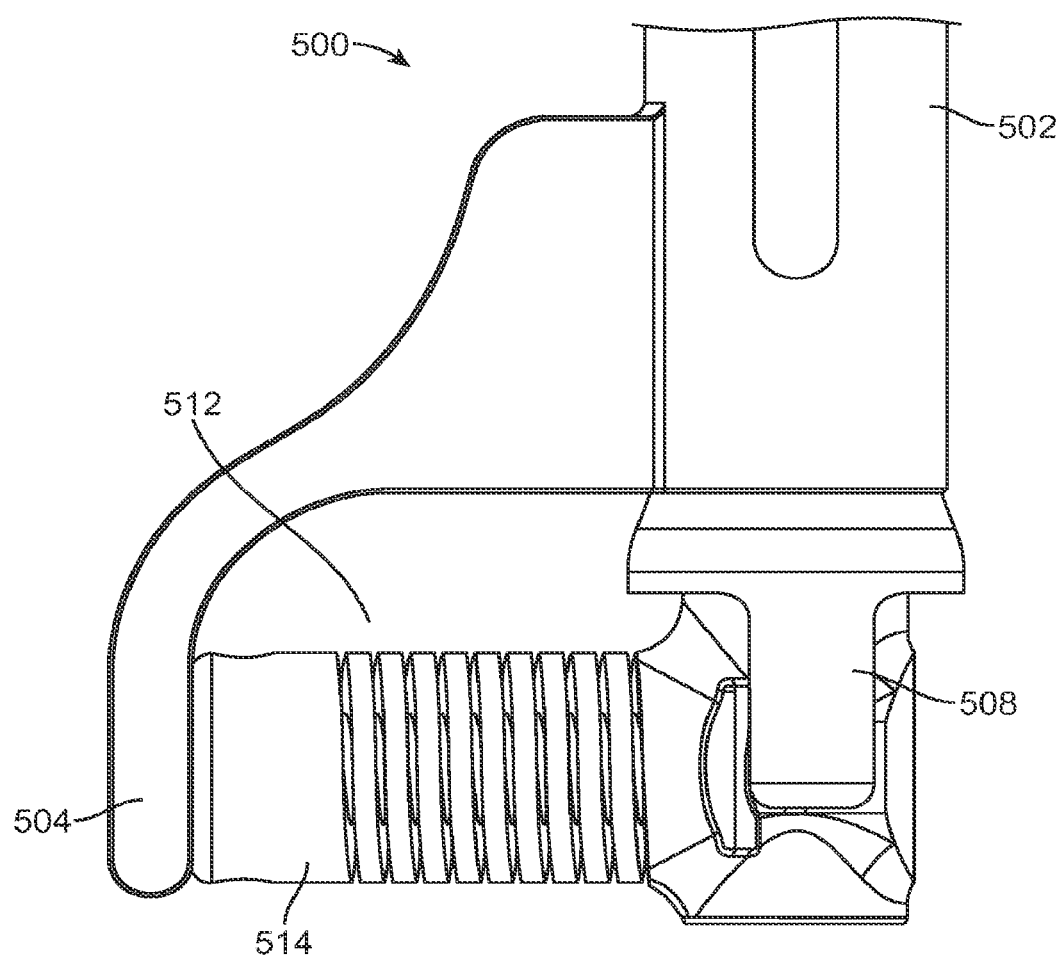
Figure 9C:
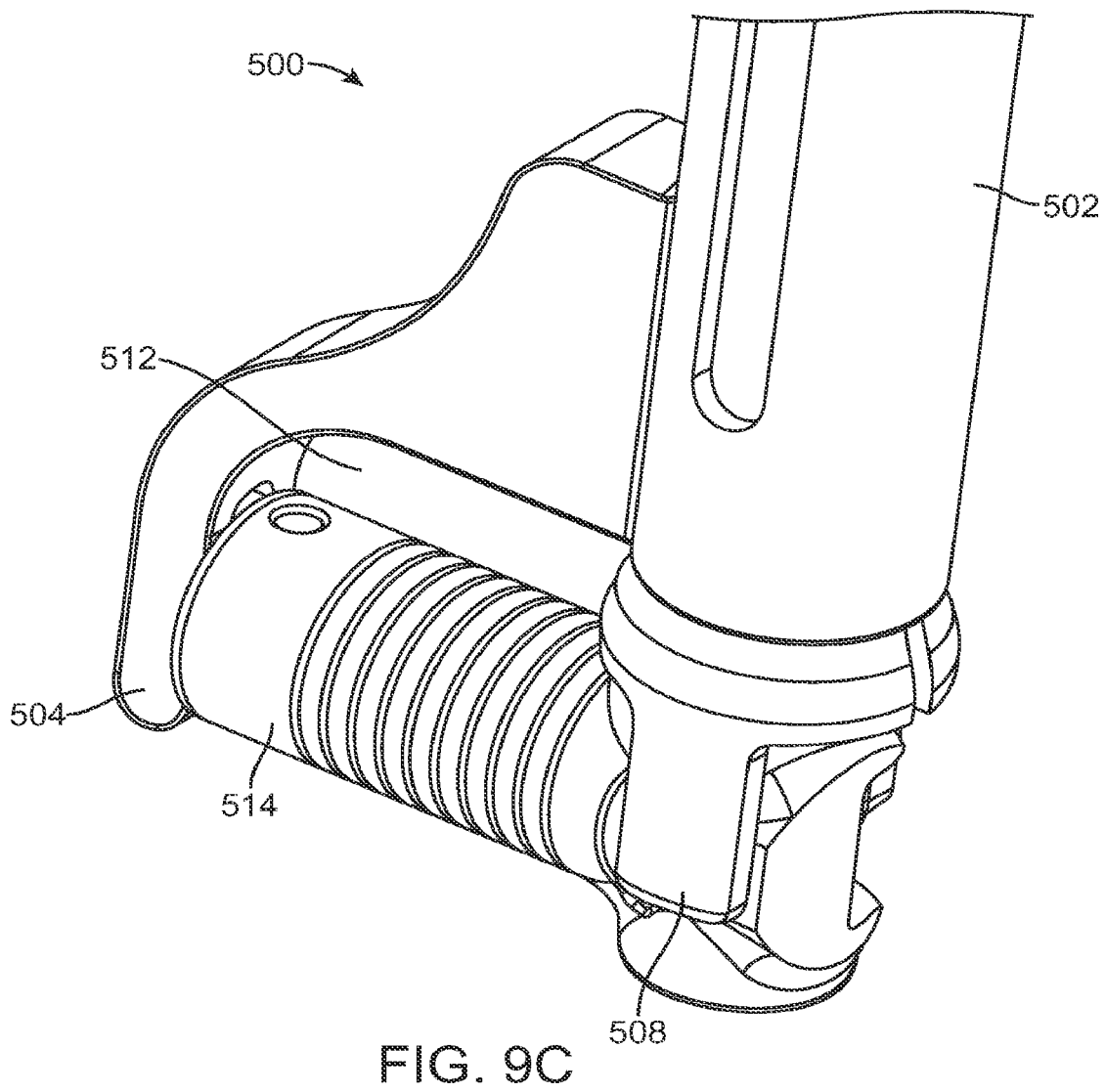

FIGS. 9A-9C illustrate an exemplary embodiment of a constraining tool 500 adapted to hold the compliance element 514 during adjustment of the spinous process constraint device. In FIG. 9A, a plurality of arms 504, 506, 508, 510 extend from an elongate shaft 502 to define a cradle or receptacle 512 for receiving the compliance element 514. The compliance element 514 is placed or snap fit in the cradle 512 and the arms 504, 506, 508, 510 engage opposite ends of the compliance element 514 and prevent expansion thereof. In other embodiments, the cradle size may be variable or sized larger than the compliance element in order to allow a pre-determined amount of extension. Additionally, the plurality of arms 504, 506, 508, 510 are spaced apart sufficiently to allow easy access to adjustment screws or apertures on the compliance element 514. The constraining tool 500 may be fabricated from any number of metals such as titanium, stainless steel or polymers such as ABS that are commonly used for surgical instruments. FIG. 9B shows a side view of the constraining tool 500 with a compliance element 514 disposed in the cradle 512. FIG. 9C illustrates a perspective view of FIG. 9B. Arms 504, 506, 508, 510 preferably do not interfere with operation of the device or affect sizing, for example by interfering with the behavior of the constraint device or offsetting the constraint device away from the spinous processes.

Figure 10A:
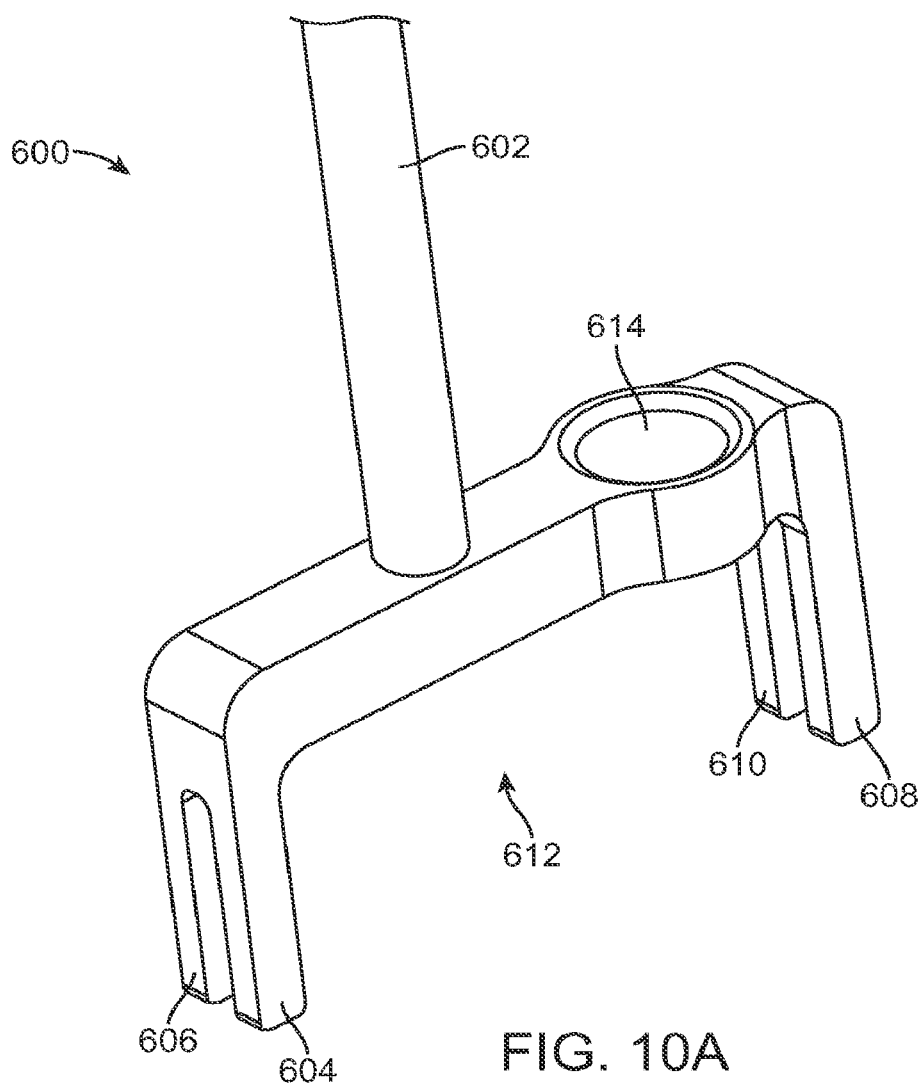
FIGS. 10A-10C illustrate another exemplary embodiment of a constraining tool.
Figure 10B:
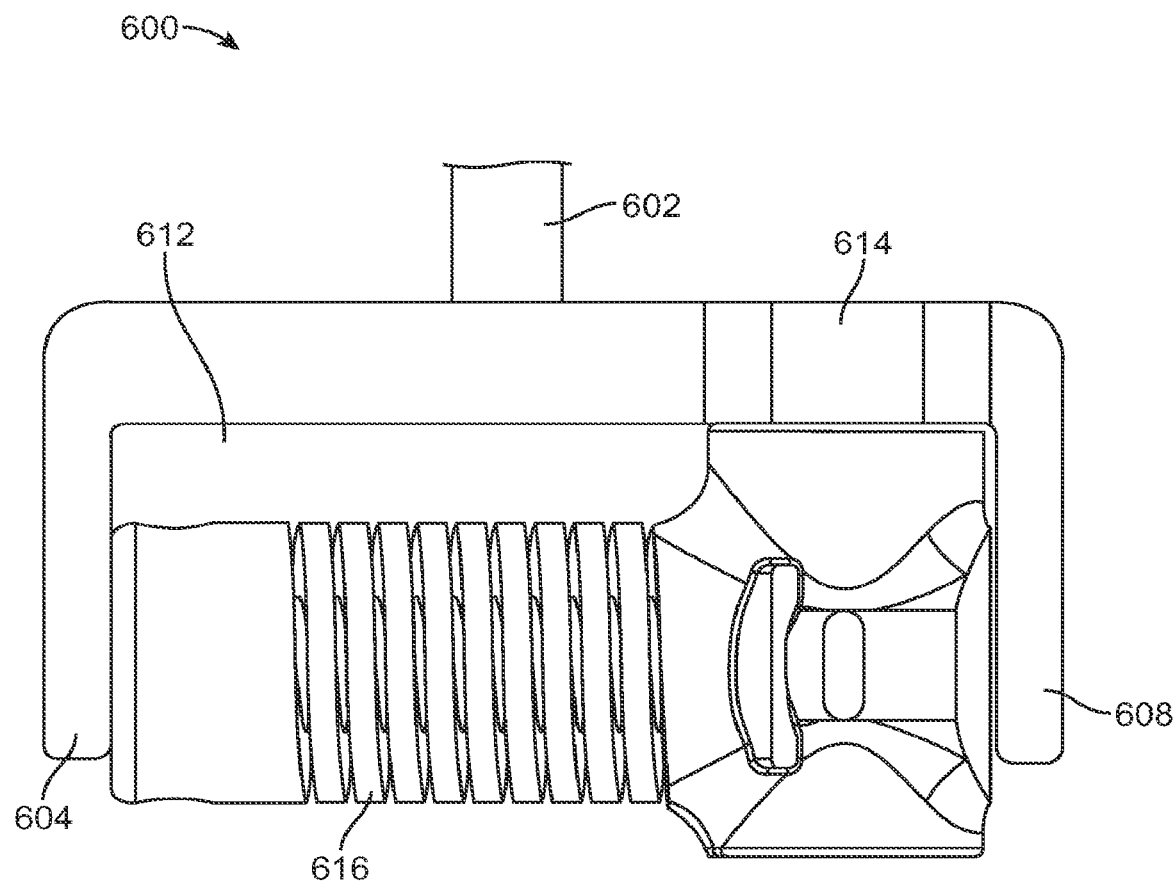
Figure 10C:
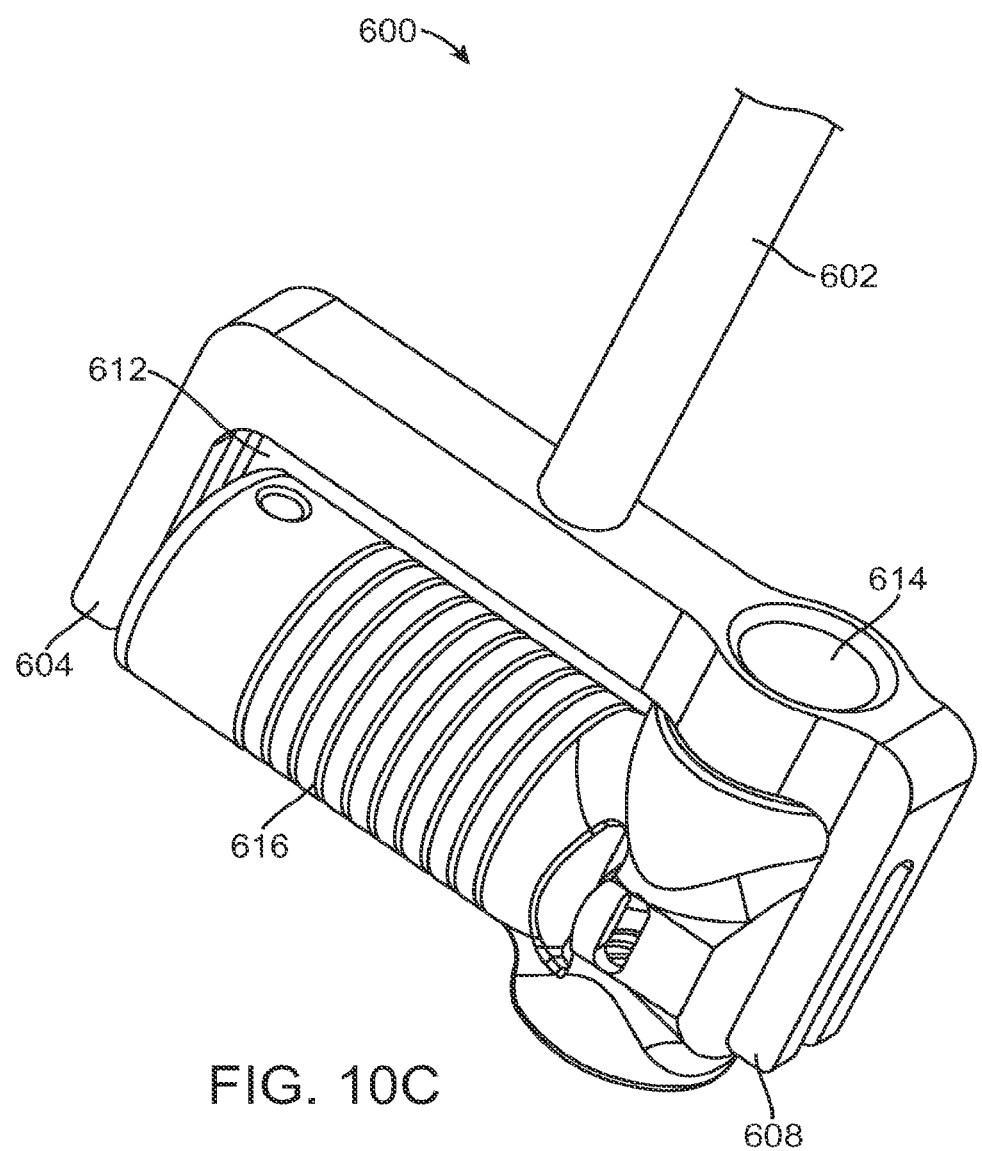

Another exemplary embodiment of a constraining tool 600 is illustrated in FIGS. 10A-10C. In FIG. 10A, constraining tool 600 includes an elongate shaft 602 and a frame having a plurality of axially extending arms 604, 606, 608, 610. The plurality of arms 604, 606, 608, 610 define a cradle or receptacle 612 for holding a compliance element 616. The cradle 612 is sufficiently open to allow easy access to the compliance element including any adjustment screws and apertures that may be included with the compliance element. Additionally, aperture 614 also allows access to the locking mechanism of compliance element 616. The locking mechanism may comprise a locking roller, details of which are disclosed in U.S. patent application Ser. No. 12/479,016, the entire contents of which have previously been incorporated herein by reference. The constraining tool 600 may be fabricated from any of the materials disclosed above with reference to FIGS. 9A-9C. FIG. 10B illustrates a side view of the constraining tool 600 with compliance element 616 disposed in the cradle 612 and FIG. 10C is a perspective view of FIG. 10B.

Figure 21A:
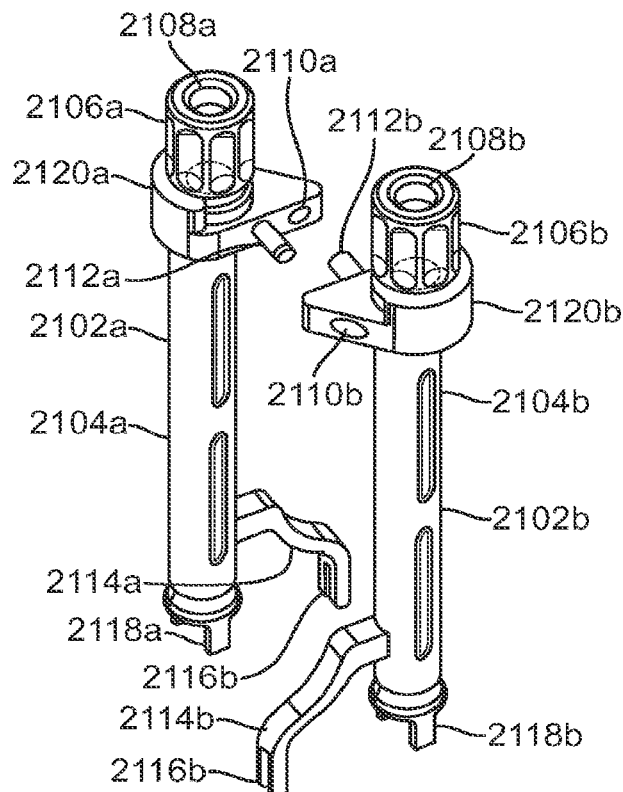
FIGS. 21A-21C illustrate an exemplary tool for constraining two compliance elements.
Figure 21B:
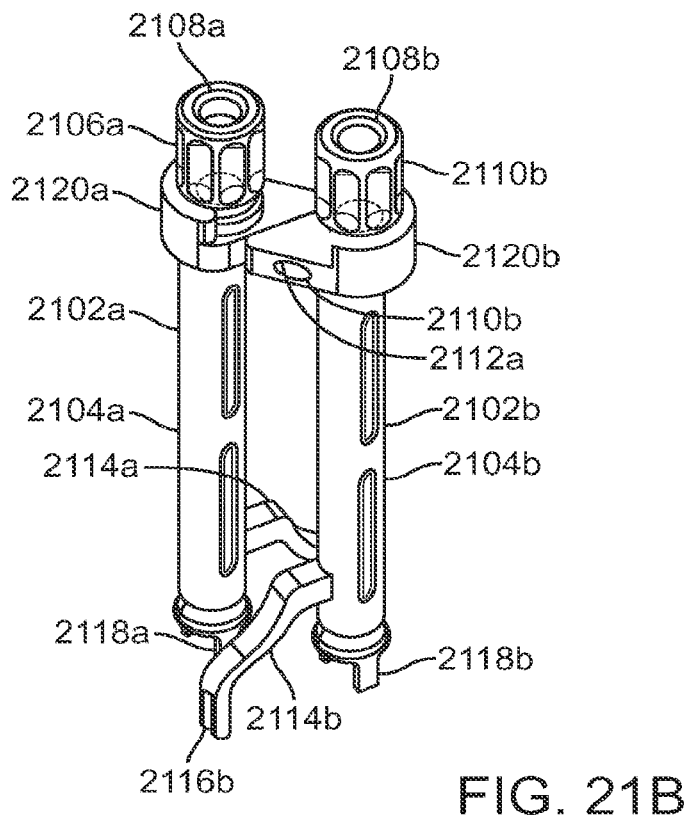
Figure 21C:
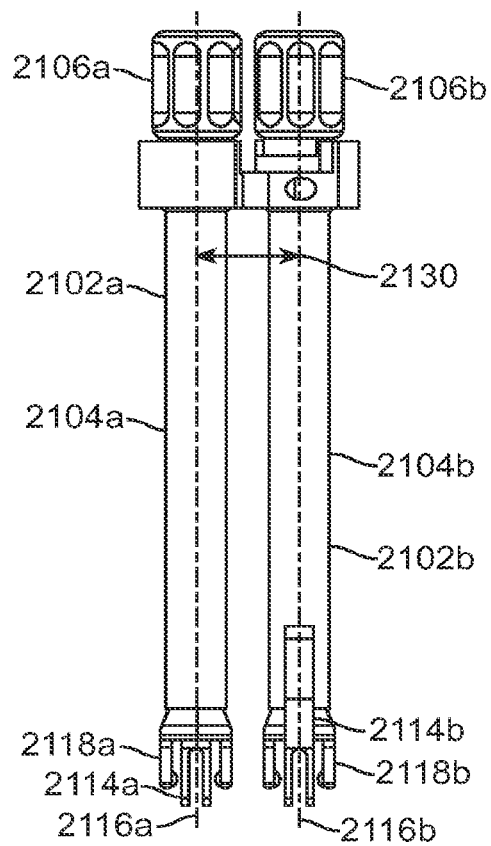

In embodiments where the constraint device has two compliance elements, it is advantageous to have two constraining tools that can simultaneously restrict movement of both the compliance elements during adjustment. FIGS. 21A-21C illustrate an exemplary embodiment of such a tool. The tool includes two constraining tools 2102a, 2102b that mate together. Each tool includes an elongate tubular shaft 2104a, 2104b with a rotatable knob 2106a, 2106b near the proximal end. The tubular shaft may be a tapered shaft that is threadably coupled with the knob such that rotating the knob advances or retracts the shaft. Thus, when the shaft is retracted, the arms 2118a, 2118b will compress and close around the compliance element.

Figure 22:
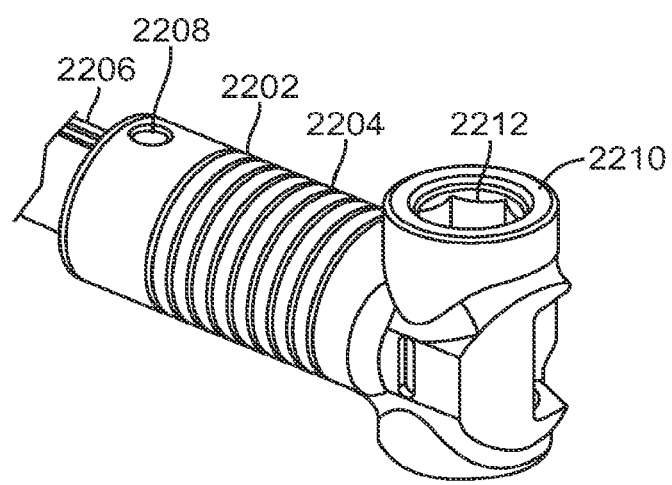
FIG. 22 illustrate an exemplary compliance element.

A central lumen 2108a, 2108b extends from the proximal end of the shaft to the distal end of the shaft and tools may be positioned in the central lumen as will be discussed below. A flanged region 2120a, 2120b near the proximal end of each shaft includes a pin 2112a, 2112b and an aperture 2110a, 2110b. The pin of one tool may be positioned in the aperture of the opposite tool thereby releasably coupling the two tools together and holding them substantially parallel to one another. The distal end of the shaft includes an arm 2114a, 2114b extending radially outward from the shaft and having a slotted region 2116a, 2116b. The distal end of the shaft also has a second arm 2118a, 2118b. The two arms on each tool form a cradle for receiving the compliance element of the constraint device and restricting expansion thereof during adjustment. The flanged region 2120a, 2120b may be sized to accommodate different patient anatomies, but in preferred embodiments, the longitudinal axes of the two tools are separated by a distance 2130 (best seen in FIG. 21C) adequate to straddle a spinous process or interspinous/supraspinous ligament complex. This distance may vary depending on the patient, but in preferred embodiments may be 10 mm to 25 mm, and more preferably 15 mm to 20 mm wide. Additionally, by using the pin-aperture coupling mechanism described above, the two tools still have one degree of freedom and can be moved in the medial-lateral directions. The compliance element is held in the cradle such that the lumen is lined up with adjustment features on the compliance element. For example, FIG. 22 illustrates an exemplary embodiment of a compliance element 2202 having a helical spring-like body 2204. A pin 2208 on one end of the compliance element secures the tether structure 2206 of the compliance device thereto and the opposite end includes a locking screw 2212 and an tether adjustment rolling mechanism (not illustrated) in the compliance element housing 2210. When the locking screw 2212 is loosened, a tool may be inserted into the housing to rotate the rolling mechanism thereby tightening or loosening the tether which passes therethrough. Once the adjustment is completed, the locking screw may be tightened to lock the roller in place, fixing tether length or tension. These features may be accessed by passing a tool (e.g. a screw driver, hex driver, etc.) through the lumen of the constraint device shaft, where they will line up concentrically with the locking screw or roller mechanism. Another advantage of the constraint tool is that it will provide a counter torque during the process of tightening the roller mechanism and the locking screw.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A system for restricting flexion of a spinal segment in a spine of a patient, said system comprising:
 a tether structure adapted to be coupled with the spinal segment or the spine;
 a first compliance element coupled with the tether structure and configured to elastically elongate as tension is applied through the tether structure; and
 a first constraining tool releasably coupled with the first compliance element so as to hold the first compliance element in a first desired position and allow a first predetermined amount of elastic elongation of the first compliance element as tension is applied to the first compliance element through the tether structure.

2. The system of claim 1, wherein the first constraining tool comprises a cradle adapted to releasably hold the first compliance element.

3. The system of claim 1, wherein the first constraining tool comprises a plurality of elongate arms, the plurality of arms forming a constraint to elongation of the first compliance element.

4. The system of claim 1, wherein the first constraining tool applies a compressive force to the first compliance element.

5. The system of claim 1, wherein the first constraining tool limits extension or elongation of the first compliance element after the first compliance element has extended or elongated by the first pre-determined amount.

6. The system of claim 1, wherein the first constraining tool is adjustable so as to vary the desired position, tension or a range of the elastic elongation of the first compliance element.

7. The system of claim 1, further comprising:
 a second compliance element coupled with the tether structure and configured to elastically elongate as tension is applied through the tether structure; and
 a second constraining tool releasably coupled with the second compliance element so as to hold the second compliance element in a second desired position and allow a second predetermined amount of elastic elongation of the second compliance element as tension is applied to the second compliance element through the tether structure, and
 wherein the first and the second constraining tools are releasably and symmetrically coupled together so as to facilitate alignment and positioning of the first and the second compliance elements on opposite sides of a midline of the spinal segment.

8. The system of claim 7, wherein the first and the second constraining tools are movable relative to one another along one degree of freedom, thereby accommodating varying thicknesses of the spinal segment or the spine.

9. The system of claim 7, wherein the first or the second compliance element comprises a locking mechanism, and at least one of the first or the second constraining tools comprise an elongate shaft having a lumen adapted to receive and align a driver or other tool concentrically with the locking mechanism.

10. The system of claim 7, wherein the first or the second compliance element releasably locks with the first or the second constraining tool.

11. A system for restricting flexion of a spinal segment in a spine of a patient, said system comprising:
 a first compliance element configured to be operably coupled with the spinal segment or the spine, the first compliance element configured to elastically elongate as tension is applied thereto; and
 a first constraining tool releasably coupled with the first compliance element so as to hold the first compliance element in a first desired position and allow a first predetermined amount of elastic elongation of the first compliance element as tension is applied to the first compliance element.

12. The system of claim 11, wherein the first constraining tool comprises a cradle adapted to releasably hold the first compliance element.

13. The system of claim 11, wherein the first constraining tool comprises a plurality of elongate arms, the plurality of arms forming a constraint to elongation of the first compliance element.

14. The system of claim 11, wherein the first constraining tool applies a compressive force to the first compliance element.

15. The system of claim 11, wherein the first constraining tool limits extension or elongation of the first compliance element after the first compliance element has extended or elongated by the first pre-determined amount.

16. The system of claim 11, wherein the first constraining tool is adjustable so as to vary the desired position, tension or a range of the elastic elongation of the first compliance element.

17. The system of claim 11, further comprising:
a second compliance element adjacent the first compliance element, the second compliance element configured to be operably coupled with the spinal segment or the spine, and configured to elastically elongate as tension is applied thereto; and
a second constraining tool releasably coupled with the second compliance element so as to hold the second compliance element in a second desired position and allow a second predetermined amount of elastic elongation of the second compliance element as tension is applied to the second compliance element, and
wherein the first and the second constraining tools are releasably and symmetrically coupled together so as to facilitate alignment and positioning of the first and the second compliance elements on opposite sides of a midline of the spinal segment.

18. The system of claim 17, wherein the first and the second constraining tools are movable relative to one another along one degree of freedom, thereby accommodating varying thicknesses of the spinal segment or the spine.

19. The system of claim 17, wherein the first or the second compliance element comprises a locking mechanism, and at least one of the first or the second constraining tools comprise an elongate shaft having a lumen adapted to receive and align a driver or other tool concentrically with the locking mechanism.

20. The system of claim 17, wherein the first or the second compliance element releasably locks with the first or the second constraining tool.

* * * * *